United States Patent [19]

Ainsworth et al.

[11] Patent Number: 5,153,210

[45] Date of Patent: Oct. 6, 1992

[54] COMPOUNDS

[75] Inventors: Anthony T. Ainsworth, Harlow; David G. Smith, Epsom, both of England

[73] Assignee: Beecham Group p.l.c., Brentford, England

[21] Appl. No.: 453,055

[22] Filed: Dec. 13, 1989

Related U.S. Application Data

[63] Continuation of Ser. No. 932,320, Nov. 19, 1986, abandoned.

Foreign Application Priority Data

Nov. 21, 1985 [GB] United Kingdom ............... 8528633

[51] Int. Cl.$^5$ ................ C07D 277/34; A61K 31/425
[52] U.S. Cl. ..................................... 514/369; 548/183
[58] Field of Search ...................... 548/183; 514/369

[56] References Cited

U.S. PATENT DOCUMENTS

| | | | |
|---|---|---|---|
| 4,287,200 | 9/1981 | Kawamatsu | 548/183 |
| 4,725,610 | 2/1988 | Meguro | 514/369 |

FOREIGN PATENT DOCUMENTS

| | | | |
|---|---|---|---|
| 0239309 | 9/1987 | European Pat. Off. | |
| 0261763 | 3/1988 | European Pat. Off. | |
| 277836 | 8/1988 | European Pat. Off. | 548/183 |
| 295828 | 12/1988 | European Pat. Off. | 548/183 |
| 1938546 | 3/1970 | Fed. Rep. of Germany | |

*Primary Examiner*—Robert Gerstl
*Attorney, Agent, or Firm*—Hopgood, Calimafde, Kalil, Blaustein & Judlowe

[57] ABSTRACT

A compound of the general formula (I):

$$R^o-X-\underset{*}{\overset{OH}{\underset{|}{C}}}HCH_2-N-\underset{\underset{R^3}{|}}{\overset{R^1}{\underset{|}{C}}}\overset{R^2}{\underset{**}{-}}(CH_2)_n-Y \quad (I)$$

(with ring A bearing $R^4-R^5$)

or a pharmaceutically acceptable ester thereof; or a pharmaceutically acceptable salt thereof, wherein, $R^o$ represents a substituted or unsubstituted aryl group or a substituted or unsubstituted benzofuranyl group, X represents a bond or $-O-CH_2-$, $R^1$ represents a hydrogen atom or a moiety $$R^o-X-\underset{***}{\overset{OH}{\underset{|}{C}}}HCH_2-$$

wherein $R^o$ and X are as defined above;

$R^2$ and $R^3$ independently represent a hydrogen atom or an alkyl group, n represents an integer 1 or 2, Y represents a bond or a moiety $-CH_2-O-$, moiety Ⓐ represents an aryl group, $R^4$ represents a linking group, and $R^5$ represents a substituted or unsubstituted, monocyclic or fused ring heterocyclic group, having up to four heteroatoms in each ring selected from, oxygen, nitrogen and sulphur; provided that $R^5$ is not N-piperazinyl, N-piperadinyl, N-homopiperadinyl, N-pyrrolidinyl or N-morpholinyl; pharmaceutical compositions containing such compounds and their use in medicine and agriculture.

9 Claims, No Drawings

COMPOUNDS

This application is a continuation of application Ser. No. 932,320 filed Nov. 19, 1986, now abandoned.

The invention relates to a group of secondary or tertiary amine heterocyclic derivatives having β-agonist activity, to a process for preparing such compounds and their use in medicine and agriculture.

European Patent Specification, Publication Number 0,070,133 discloses certain phenoxyalkylaminoethanolamine derivatives having inter alia anti-obesity and/or anti-hyperglycaemic activity. Some of the compounds disclosed in EP 0,070,133 are phenoxy 5-, 6-or 7- cycloalkylamino ethanolamine derivatives.

It has now been discovered that a series of novel secondary or tertiary amine heterocyclic derivatives show good β-agonist activity; they show good anti-obesity and anti-hyperglycaemic activity coupled with good selectivity from cardiac side effects.

Accordingly, the invention provides a compound of the general formula (I):

$$R^o-X-\overset{OH}{\underset{*}{C}}HCH_2-N-\overset{R^1}{\underset{R^3}{C}}\overset{R^2}{\underset{**}{-}}(CH_2)_n-Y$$

$$\overset{\displaystyle A}{\underset{R^4-R^5}{\bigcirc}}$$

or a pharmaceutically acceptable ester thereof; or a pharmaceutically acceptable salt thereof, wherein, $R^o$ represents a substituted or unsubstituted aryl group or a substituted or unsubstituted benzofuranyl group, X represents a bond or $-O-CH_2-$, $R^1$ represents a hydrogen atom or a moiety $$R^o-X-\overset{OH}{\underset{***}{C}}HCH_2-$$

wherein $R^o$ and X are as defined above;

$R^2$ and $R^3$ independently represent a hydrogen atom or an alkyl group, n represents an integer 1 or 2, Y represents a bond or a moiety $-CH_2-O-$, moiety Ⓐ represents an aryl group, $R^4$ represents a linking group, and $R^5$ represents a substituted or unsubstituted, monocyclic or fused ring heterocyclic group, having up to four heteroatoms in each ring selected from, oxygen, nitrogen and sulphur; provided that $R^5$ is not N-piperazinyl, N-piperadinyl, N-homopiperadinyl, N-pyrrolidinyl or N-morpholinyl.

Preferably, $R^o$ represents a substituted or unsubstituted aryl group.

When used herein in relation to $R^0$ and Ⓐ the term 'aryl' includes phenyl and naphthyl optionally substituted with up to five, preferably up to three, groups selected from halogen, alkyl, phenyl, alkoxy, haloalkyl, hydroxy alkyl, hydroxy, amino, nitro, carboxy and pharmaceutically acceptable salts, esters and amides thereof, alkoxycarbonyl, alkoxycarbonyl alkyl alkylcarbonyloxy, or alkylcarbonyl groups.

A preferred aryl group is a substituted or unsubstituted phenyl group.

Preferred optional substituents for the aryl group include up to three substituents selected from halogen, hydroxy, alkoxy, and hydroxy alkyl and amino.

When $R^o$ represents a benzofuranyl group it is preferably a benzofuran-2-yl group.

When the benzofuranyl group is substituted, it is preferably substituted in the phenyl ring; a suitable substituent for the phenyl ring being an alkyl group. Suitably, the phenyl ring in the benzofuranyl moiety is substituted in the 7-position, suitably with an alkyl group such as for example methyl or ethyl.

Preferably, when $R^o$ represents a benzofuranyl group X represents a bond

Suitable optional substituents for $R^5$ include alkyl; hydroxy; alkoxy; oxo; amino; alkanoyl amino; mono- and di- alkyl amino; mono- and di- alkylaminoalkyl; fluoro; chloro; bromo; carboxy and pharmaceutically acceptable salts, esters and amides thereof; alkanoyloxy; substituted or unsubstituted aryl or substituted or unsubstituted aryl alkyl.

Suitably, X represents a bond.

Favourably, $R^1$ represents a hydrogen atom.

Suitably, $R^2$ represents an alkyl group, preferably a methyl group.

Suitably, $R^3$ represents a hydrogen atom.

Suitably, $R^4$ represents a bond or an oxygen atom or $-R^{4A}$ or a moiety $-O-R^{4A}$ or a moiety $-R^{4A}-O-$, wherein $R^{4A}$ represents an alkylene group, an alkenylene group or a alkynylene group.

Preferably, $R^{4A}$ represents an alkylene group, especially $-CH_2-$.

Preferably, Y represents a bond.

Preferably the moiety $$\overset{\displaystyle A}{\underset{R^4-R^5}{\bigcirc}}$$

represents a moiety $$\overset{|}{\underset{R^4-R^5}{\bigcirc}}$$

wherein $R^4$ and $R^5$ are as defined above.

Preferably $-R^4-R^5$ is in the para position on the phenyl ring relative to the point of attachment of the phenyl ring to the rest of the molecule.

Preferably, n represents the integer 1.

Preferred hetero atoms in the heterocyclic group represented by $R^5$ are oxygen, nitrogen and sulphur Suitably, $R^5$ represents an unsaturated heterocyclic group.

In one particular aspect of the invention, the heterocyclic group represented by $R^5$ is a substituted or unsubstituted 5-, 6-or 7-membered, monocyclic heterocylic group.

Favourably, the heterocyclic group represented by $R^5$ is a substituted or unsubstituted 5-membered monocyclic heterocyclic group.

Suitable 5-membered rings represented by $R^5$ include pyrrolyl, pyrrolinyl, 2,3,4 and 5-pyrrolidinyl, furanyl, tetrahydrofuranyl, thiophenyl, pyrrolinyl, pyrazolidinyl, imidazolinyl, oxazolyl, dihydrooxazolyl, tetrahydrooxazolinyl, isoxazolyl, thiazolyl, isothiazolyl, dihyrothiazolinyl, thiazolidinyl and tetrazolyl.

Favoured 5-membered rings include pyrrolyl, pyrrolinyl, furanyl, thiophenyl, pyrazolidinyl, imidazolinyl, oxazolyl, dihydrooxazolyl, isoxazolyl, thiazolyl, isothiazolyl, dihydrothiazolinyl, thiazolidinyl and tetrazolyl.

Favourably, the heterocyclic group represented by $R^5$ is a substituted or unsubstituted 6-membered monocyclic heterocyclic group.

Suitable 6-membered rings represented by $R^5$ include pyranyl, pyridinyl, tetrahydropyridyl, pyridazinyl, pyrimidinyl, 1,2- or 1,3-oxazinyl, 2,3,5 or 6 morpholinyl and 2,3,4,5 or 6 piperidinyl.

Favourable 6-membered rings represented by $R^5$ include pyranyl, tetrahydropyranyl, pyridinyl, tetrahydropyridyl, pyridazinyl, pyrimidinyl, and oxazinyl.

A preferred 6-membered ring is the pyranyl ring.

A particularly preferred 6-membered ring is the pyran-4-one ring.

Favourably, the heterocyclic group represented by $R^5$ is a substituted or unsubstituted 7-membered monocyclic heterocyclic group.

In one aspect of the present invention, $R^5$ represents a group of the general formula (A), (B), (C) or (D):

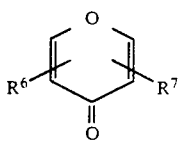 (A)

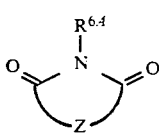 (B)

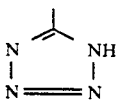 (C)

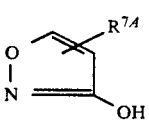 (D)

wherein $R^6$ and $R^{78}$ each independently represent a bond, a hydrogen atom, a hydroxyl group, an alkyloxy group; or a benzyloxy group; $R^{6A}$ represents a bond or a hydrogen atom or an alkyl group or a carbonylalkyl group; $R^{7A}$ represents a bond; and Z represents a moiety of formula:

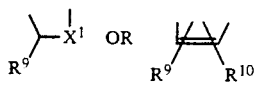

wherein $R^9$ and $R^{10}$ each independently represent a bond, a hydrogen atom, a hydroxyl group, an alkoxy group; and $X^1$ represents O, NH or S; provided that at least one of $R^6$ and $R^7$; and at least one of $R^{6A}$, $R^9$ and $R^{10}$ represents a bond.

Suitably, $R^5$ represents the hereinbefore defined group (A).

Suitably, $R^5$ represents the hereinbefore defined group (B).

Suitably, $R^5$ represents the hereinbefore defined group (C).

Suitably, $R^5$ represents the hereinbefore defined group (D).

Preferably, $R^5$ represents the hereinbefore defined group (A).

In one preferred aspect, the present invention provides a compound of formula (II):

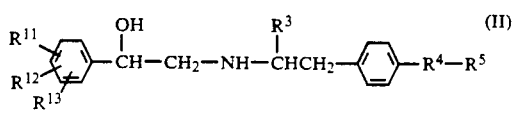 (II)

or a pharmaceutically acceptable ester thereof; or a pharmaceutically acceptable salt thereof, wherein $R^3$, $R^4$ and $R^5$ are as defined in relation to formula (I) and $R^{11}$, $R^{12}$ and $R^{13}$ each independently represent hydrogen; halogen, preferably chlorine; amino, hydroxy or hydroxymethyl.

Favourably, when $R^4$ represents a moiety of formula $OR^{4a}$ wherein $R^{4a}$ represents alkylene, $R^5$ represents a moiety of the hereinbefore defined formula (A) or (C).

Favourably, when $R^4$ represents alkylene, $R^5$ represents a moiety of the hereinbefore defined formula (B).

Favourably, when R4 represents an oxygen atom, $R^5$ represents a moiety of the hereinbefore defined formula (D).

Favourably, when $R^4$ represents a bond, $R^5$ represents a moiety of the hereinbefore defined formula (C).

Suitably, $R^{11}$ and $R^{12}$ each represent a hydrogen atom.

Suitably, $R^{11}$ and $R^{12}$ each represent a halogen atom, preferably a chlorine atom.

Favourably, $R^{11}$, $R^{12}$ and $R^{13}$ each represent a hydrogen atom.

Favourably, $R^{11}$ and $R^{12}$ each represent a hydrogen atom and $R^{13}$ represents a hydroxyl group.

Favourably, $R^{11}$ and $R^{12}$ each represent a hydrogen atom, and $R^{13}$ represents a halogen atom, preferably a chlorine atom.

Favourably, $R^{11}$ and $R^{12}$ each represent a chlorine atom and $R^{13}$ represents an amino group.

Preferably the moiety $R^{11}R^{12}R^{13}C_6H_3$—represents a group selected from the list consisting of: phenyl, 3-chlorophenyl, 4-hydroxyphenyl and 3,5-dichloro-4-aminophenyl.

Preferably, $R^3$ represents a methyl group.

Preferably, the moiety —$R^4$—$R^5$ represents a moiety selected from the list consisting of:

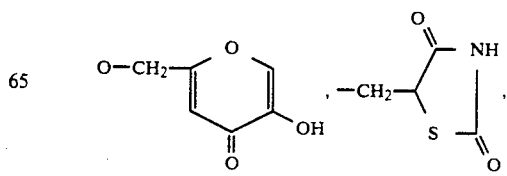

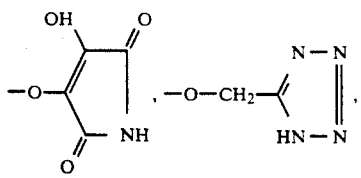
, 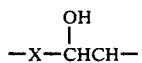

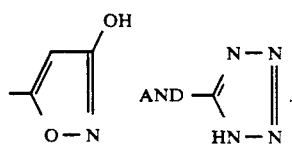

Most preferably, the moiety —R⁴—R⁵ represents

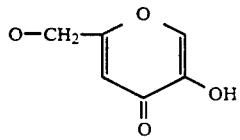

In a particularly preferred aspect the present invention provides a compound selected from the groupconsisting of:

4-[4-[2-[(3-chloro-β-hydroxyphenethyl) amino]propyl]phenoxy]-3-hydroxy-1H-pyrrole-2,5-dione;
4-[4-[2-[(β,4-dihydroxyphenethyl)amino]propyl]phenoxy]-3-hydroxy-1H-pyrrole-2,5-dione;
2-[4-[2-[(3-chloro-β-hydroxyphenethyl)amino]propyl]phenoxymethyl]-5-hydroxy-4H-pyran-4-one;
5-[4-[2-[(β-4-dihydroxyphenethyl)amino]propyl]benzyl]thiazolidine-2,4-dione;
5-[4-[2-[(3-chloro-β-hydroxyphenethyl)amino]propyl]benzyl]thiazolidine-2,4-dione;
5-[4-[2-[(4-amino-3,5-dichloro-β-hydroxyphenethyl)amino]propyl]benzyl]thiazolidine-2,4-dione;
5-[4-[2-[3-chloro-β-hydroxyphenethyl)amino]propyl]phenoxymethyl]tetrazole;
5-[4-[2-(3-chloro-β-hydroxyphenethyl)amino]propyl]phenyl]tetrazole;
5-[4-[2-(3-chloro-β-hydroxyphenethyl)amino]propyl]phenyl]-3-hydroxyisoxazole;
or a pharmaceutically acceptable ester thereof; or a pharmaceutically acceptable salt thereof.

The present invention most preferably provides 4-[4-[2-[(3-chloro-β-hydroxyphenethyl)amino]propyl]phenoxy]-3-hydroxy-1H-pyrrole-2,5-dione; or a pharmaceutically acceptable ester thereof; or a pharmaceutically acceptable salt thereof.

The present invention most preferably provides 2-[4-[2-[(3-chloro-β-hydroxyphenethyl)amino]propyl]phenoxymethyl]-5-hydroxy-4H-pyran-4-one; or a pharmaceutically acceptable ester thereof; or a pharmaceutically acceptable salt thereof.

When used herein the term "alkyl", "alkenyl", "alkynyl" or "alkoxy" relates to groups having straight or branched chains containing up to 12 carbon atoms.

Suitable alkyl groups are $C_{1-12}$ alkyl groups especially $C_{1-6}$ alkyl groups e.g. methyl, ethyl, n-propyl, iso-propyl, n-butyl, isobutyl or tert-butyl groups.

Suitable alkenyl groups are $C_{2-12}$ groups especially $C_{2-6}$ alkenyl groups.

Suitable alkynyl groups are $C_{2-12}$ alkynyl groups especially $C_{2-6}$ alkynyl groups.

When used herein the term "halogen" refers to fluorine, chlorine, bromine and iodine, preferably chlorine.

The hydroxy group present in the moiety $$-X-\underset{|}{CHCH}-$$
$$\phantom{-X-}OH$$

or any hydroxyl group present in the moiety $R^o$ or $R^5$ may be derivatised as an ester, by for example, an arylalkyl carboxylic acid or a $C_{1-6}$- alkyl carboxylic acid. Suitable esters are in-vivo hydrolysable esters. Such esters and pharmaceutically acceptable salts of such esters form further aspects of the present invention.

When used herein the term "in-vivo hydrolysable ester" relates to a pharmaceutically acceptable ester which readily breaks down in the human or non-human animal body to leave the free hydroxy group. Suitable in-vivo hydrolysable ester groups are those used conventionally in the art; they are preferably those provided by lower alkyl carboxylic acids.

The present invention also encompasses the salts of hydroxyl groups in for example $R^5$. Suitable such salts are metal salts especially alkali metal salts for example sodium salts.

Preferably the above mentioned hydroxyl groups are present as free hydroxyl groups.

The compounds of the general formula (I) may have, depending on the meaning of $R^1$, $R^2$, $R^3$ and $R^5$, up to four asymmetric carbon atoms, marked with asterisks in the formula. These compounds may, therefore, exist in up to sixteen stereoisomeric forms. The present invention encompasses all stereoisomers of the compounds of the general formula (I) whether free from other isomers or admixed with other isomers in any proportion, and thus includes for instance, racemic mixtures of enantiomers.

The absolute configuration of any compound of the general formula (I) may be determined by conventional X-ray crystallographic techniques.

Suitably, when $R^2 \neq R^3$, the '**' asymmetric carbon has the R-configuration.

Suitably, when X represents a bond, the '*' asymmetric carbon has the R configuration.

Suitably, when X represents —O—CH₂, the '*' asymmetric carbon has the S-configuration.

Suitably, when X represents a bond, the '***' asymmetric carbon has the R-configuration.

Suitably, when X represents —O—CH₂ the '***' asymmetric carbon has the S-configuration.

When $R^1$=H and $R^2 \neq R^3$, a preferred enantiomer of the compounds of formula (I) is that wherein the asymmetric carbons have the following configurations:

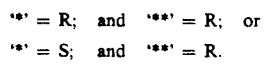

When $R^1 \neq H$ and $R^2 \neq R^3$, a preferred enantiomer of the compound of formula (I) is that wherein the asymmetric carbons have the following configurations:

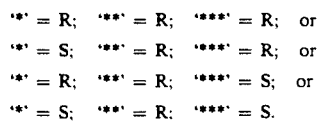

Suitable pharmaceutically acceptable salts of the compounds of formula (I) include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Compounds of the general formula (I) also form acid addition salts.

Pharmaceutically acceptable acid addition salts may be, for example, salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid or acetylsalicylic acid.

Pharmaceutically acceptable amides include amides of formula —CONR$^s$R$^t$ wherein R$^s$ and R$^t$ each independently represents hydrogen or C$_{1-6}$ alkyl, or R$^s$ and R$^t$ together with the nitrogen atom to which they are attached form a saturated 5- or 6- membered ring.

Solvates, preferably hydrates, of the compound of formula (I) are also encompassed by the invention.

The invention also provides a process for the preparation of a compound of the general formula (I) or a pharmaceutically acceptable ester thereof; or a pharmaceutically acceptable salt thereof, which comprises either:

(A) reacting a compound of the general formula (III)

$$R^o-X-Q \qquad (III)$$

wherein R$^o$ and X are as defined in relation to formula (I) and Q represents a group of formula (a) or (b):

(a)       (b)

wherein

R$^{14}$ represents a hydroxyl group or a protected hydroxyl group, and X$^1$ represents a leaving group, with a compound of the general formula (IV):

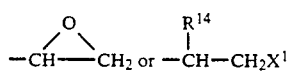

wherein (A), R$^4$, R$^5$, n and Y are as defined in relation to formula (I), and Q$^1$ represents a group of the formula (F):

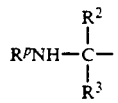

wherein R$^2$ and R$^3$ are as defined in relation to formula (I), and R$^p$ represents a hydrogen atom, a protecting group, preferably a benzyl group, or the hereinbefore defined moiety R$^1$; or in the abovementioned compound of formula (III) Q represents a group of the formula (c):

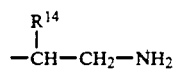

wherein R$^{14}$ has the meaning given above, and in the abovementioned compound of formula (IV) Q$^1$ represents a group of the formula (g):

in which R$^2$, R$^3$ and X$^1$ have the meanings given above; or (B) for compounds of formula (I) wherein R$^1$ represents only the moiety

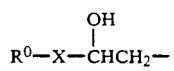

as defined above, by reacting a compound of formula (I) wherein R$^1$ represents a hydrogen atom, with either:

(i) a compound of formula (IIIA):

$$R^o-X-Q \qquad (IIIA)$$

wherein R$^o$ and X are as defined in relation to formula (I) and Q represents a group of the hereinbefore defined formula (a) or (b); or (ii) a compound of formula (V):

$$R^0-X-CO-CHO \qquad (V)$$

wherein R$^o$ and X are as defined in relation to formula (I); and subsequently treating with a reducing agent; or (iii) a compound of formula (VI):

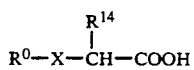

wherein R$^o$ and X are as defined in relation to formula (I) and R$^{14}$ represents a hydroxyl group or a protected hydroxyl group; and subsequently reducing the resulting hydroxyamide; and thereafter if necessary carrying out one or more of the following steps;

i) removing any protecting group;
ii) converting a compound of formula (I) into a further compound of formula (I);
iii) converting a salt of formula (I) into a free compound of formula (I);

iv) preparing a pharmaceutically acceptable ester of a compound of formula (I);

v) preparing a pharmaceutically acceptable salt of a compound of formula (I) or an ester thereof.

The present invention also provides a process for the preparation of a compound of the general formula (I) or a pharmaceutically acceptable ester thereof; or a pharmaceutically acceptable salt thereof, which comprises reducing a compound of the general formula (VII):

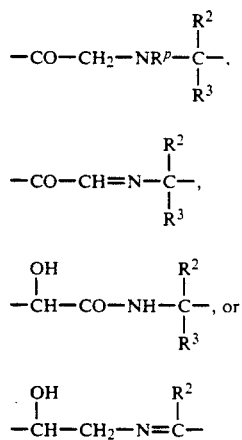    (VII)

in which $R^o$, (A), $R^4$, $R^5$, X, Y and n are as defined in relation to formula (I), and $R^t$ represents a group of formula:

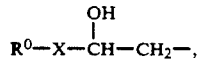

in which $R^p$ is hydrogen or a protecting group, preferably a benzyl group, $R^2$ and $R^3$ are as defined in relation to formula (I);

and if required converting a compound of formula (I) wherein $R^1$ represents hydrogen into a compound of formula (I) wherein $R^1$ represents a moiety of formula $$R^o-X-\overset{OH}{\underset{|}{CH}}-CH_2-,$$

wherein $R^o$ and X are as defined above, by reacting the compound of formula (I) wherein $R^1$ represents hydrogen with a compound of formula (IIIA), (V) or (VI) as described hereinbefore; and thereafter if necessary carrying out one or more of the following steps;

i) removing any protecting group;

ii) converting a compound of formula (I) into a further compound of formula (I);

iii) converting a salt of formula (I) into a free compound of formula (I);

iv) preparing a pharmaceutically acceptable ester of a compound of formula (I);

v) preparing a pharmaceutically acceptable salt of a compound of formula (I) or an ester thereof.

The starting materials of the general formula (VII) may be prepared, for example, by reacting compounds of the general formulae (III) and (IV) in which: $R^o$ and X are as defined in relation to formula (III) and Q represents a group of the formula (d), (e) or (f):

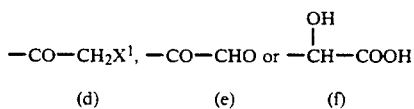

wherein $X^1$ is as defined in relation to formula (III), and $Q^1$ represents a group of the formula ($F^1$)

wherein $R^2$ and $R^3$ are as defined in relation to formula (I) and $R^p$ is a hydrogen atom or a benzyl group; or, in the case of compounds of formula (VII) wherein $R^3$ represents hydrogen, Q represents a group of the formula (c):

and $Q^1$ represents a group of the formula (J):

in which $R^2$ has the meaning given above.

Any protecting groups used in the above reactions are those used conventionally in the art. For example when $R^o$ represents a phenyl group substituted with a hydroxy group, any conventional hydroxy protecting group may be used. Preferably the hydroxy group being protected by etherification; the ether group being converted into a free hydroxy group by methods known per se. For example, an unsubstituted or substituted benzyloxy protecting group, may be converted by hydrogenolysis into a free hydroxy group. The hydrogenolysis reaction may be carried out, for example in the presence of a palladium-on-carbon catalyst in a solvent, for example a mixture of ethyl acetate and methanol.

A leaving group $X^1$ is any group that will, under the reaction conditions, cleave from the starting material, thus promoting reaction at a specified site. Suitable examples of such groups are halogen atoms, mesyloxy groups and tosyloxy groups. Preferably in formula (b) of compound (III) or in formula (g) of compound (IV) $X^1$ represents a mesyloxy or tosyloxy group or a bromine atom, and in formula (d) of compound (III) $X^1$ represents a bromine atom.

Compounds of formulae (III), (IIIA) and (IV) are either known compounds or can be prepared from known compounds by known processes or processes analogous to known processes.

The reaction of compounds of the general formulae (III) and (IV) in which Q and $Q^1$ have formulae (a) and (F) respectively is advantageously carried out in a protic solvent, e.g. an alkanol, especially a lower alkanol having at least 2 carbon atoms, at reflux, preferably in ethanol. The reaction between the compounds of formula (I) (wherein $R^1=H$) and (IIIA) (wherein $Q=(a)$) may be carried out under similar conditions.

Reaction of compounds of the general formulae (III) and (IV) in which Q and $Q^1$ have formulae (b) and (F) or (c) and (G) respectively is advantageously carried out in dimethyl sulphoxide, for example at a temperature in the range of from 30° to 80° C., e.g. substantially 50° C., and advantageously for a period of time of 1 to 4 days, e.g. about 3 days. The reaction between the compounds of formula (I) (wherein $R^1=H$) and (IIIA) (wherein $Q=(b)$) may be carried out under similar conditions.

The reaction of the compounds of the general formulae (III) and (IV) in which Q and $Q^1$ have formulae (d) and (F) respectively is advantageously carried out in butanone or acetonitrile at reflux, if desired in the presence of a base.

The reaction of compounds of the general formula (III) and (IV) in which Q and $Q^1$ have formulae (e) and (F) or (c) and (J) respectively is preferably carried out in benzene using a Dean and Stark apparatus, more especially at reflux.

The reaction of compounds of the general formulae (III) and (IV) in which Q and $Q^1$ have formulae (f) and (F) respectively is preferably carried out in the presence of dicyclohexyl carbodiimide or other suitable condensing agent.

The reduction of a compound of the general formula (VII) may be carried out, for example, when $R'$ represents a group of the formula (i) and (ii) with sodium borohydride; when $R'$ represents a group of the formula (iii) with a borane reducing agent, for example borane methyl sulphide complex, and when $R'$ represents a group of the formula (iv) with sodium borohydride or sodium cyanoborohydride, or catalytically, for example by hydrogen in the presence of platinum or palladium.

The reaction between the compounds of formula (I) (wherein $R^1=H$) and (V) is preferably carried out in methanol at ambient temperature, the subsequent reduction being carried out, for example, with sodium cyanoborohydride.

The reaction between the compounds of formula (I) (wherein $R^1=H$) and (VI) is preferably caried out in the presence of dicyclohexyl carbodiimide or other suitable condensing agent; the subsequent reduction may be carried out with, for example, lithium aluminium hydride or a borane reducing agent, for example borane methyl sulphide complex.

The reductions with sodium cyanoborohydride and sodium borohydride are preferably performed in a lower alkanol, e.g. methanol.

In a further aspect the present invention provides a process for the preparation of a compound of formula (I) or a pharmaceutically acceptable ester thereof; or a pharmaceutically acceptable salt thereof, from a compound of formula (VIII):

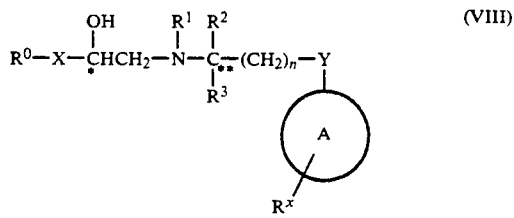
(VIII)

wherein $R^0$, (A), $R^1$, $R^2$, $R^3$, X, n and Y are as defined in relation to formula (I) and $R^x$ is a moiety convertible to a moiety $—R^4—R^5$; and thereafter if necessary carrying out one or more of the following steps;
  i) removing any protecting group;
  ii) converting a compound of formula (I) into a further compound of formula (I);
  iii) converting a salt of formula (I) into a free compound of formula (I);
  iv) preparing a pharmaceutically acceptable ester of a compound of formula (I);
  v) preparing a pharmaceutically acceptable salt of a compound of formula (I) or an ester thereof.

Suitable moieties $R^x$ are those which are convertible to moieties $—R^4—R^5$ by conventional methods, for example:

(1) $R^x$ may represent a moiety $R^4—CN$, wherein $R^4$ is as defined in relation to formula (I), which may be treated with an azide, such as ammonium azide, thereby converting the moiety $R^4—CN$ to a moiety $—R^4—R^5$ wherein $R^5$ is tetrazolyl.

(2) $R^4$ may represent $R^4—CO_2H$, or a salt or ester thereof, wherein $R^4$ is as defined in relation to formula (I), which may be treated with an amino alkylamine, wherein the amino groups are attached to different carbon atoms; for example 1,2 - diamino ethane converts $R^4—CO_2H$ to a moiety $—R^4—R^5$ wherein $R^5$ is imidazolyl. In a similar fashion $R^4\text{-}CO_2H$ may be treated with an amino alkylthiol wherein the thiol and amino groups are attached to different carbon atoms; for example 2-amino ethane thiol converts $R^4\text{-}CO_2H$ to a moiety $—R^4—R^5$ wherein $R^5$ is 4,5-dihydrothiazolyl. Reaction (1) above is conveniently carried out in an aprotic solvent such as dimethylformamide, suitably at an elevated temperature, such as 100° C.

Reaction (2) above is conveniently carried out in an inert solvent such as toluene, suitably at an elevated temperature such as the reflux temperature of the chosen solvent; the reaction is preferably carried out in the presence of a catalyst such as tri-isobutylaluminium.

Compounds of the hereinbefore defined compound of formula (VIII) may be prepared where appropriate by analogous methods to those used for the compounds of formula (I).

In a preferred method of preparing a compound of the general formula (I) wherein $R^1$ represents hydrogen, or a pharmaceutically acceptable ester thereof; or a pharmaceutically acceptable salt thereof, a compound of formula (IIIc):

$$\underset{R^0-\overset{|}{C}H-CH_2-NH_2}{OH} \qquad (IIIc)$$

wherein $R^0$ is as defined in relation to formula (I), is reacted with a compound of the general formula (IVJ):

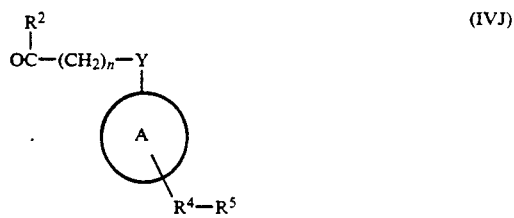
(IVJ)

wherein (A), $R^2$, $R^4$, $R^5$, Y, and n are as defined relation to formula (I), to provide a compound of the general formula (VII) wherein R' represents a group of the general formula (iv): the said compound of formula (VII) is then reduced with sodium cyanoborohydride, preferably in methanol; and thereafter if necessary carrying out one or more of the following steps;

i) removing any protecting group;
ii) converting a compound of formula (I) into a further compound of formula (I);
iii) converting a salt of formula (I) into a free compound of formula (I);
iv) preparing a pharmaceutically acceptable ester of a compound of formula (I);
v) preparing a pharmaceutically acceptable salt of a compound of formula (I) or an ester thereof.

The salts of compounds of the general formula (I) may be produced by methods conventional in the art, for example, acid addition salts may be prepared by treating a compound of general formula (I) or pharmaceutically acceptable esters thereof with the appropriate acid.

Compounds of the general formula (I) or pharmaceutically acceptable esters thereof and salts thereof, produced by the above processes, may be recovered by conventional methods.

Compounds of the general formula (I) may be separated into diastereoisomeric pairs of enantiomers by, for example, fractional crystallisation from a suitable solvent, for example methanol or ethyl acetate or a mixture thereof. The pair of enantiomers thus obtained may be separated into individual stereoisomers by conventional means, for example by the use of an optically active acid as a resolving agent. Suitable optically active acids which maybe used as resolving agents are described in 'Topics in Stereochemistry', Vol. 6, Wiley Interscience, 1971, Allinger, N.L. and Eliel, W.L. Eds.

Alternatively, any enantiomer of a compound of the general formula (I) may be obtained by stereospecific synthesis using optically pure starting materials of known configuration.

As previously indicated, the compounds of the present invention have valuable pharmacological properties.

The present invention also provides a compound of the general formula (I) or a pharmaceutically acceptable ester; or a pharmaceutically acceptable salt thereof for use as an active therapeutic substance.

In one aspect, the present invention provides a compound of the general formula (I) or a pharmaceutically acceptable ester thereof; or a pharmaceutically acceptable salt thereof for use in the treatment of obesity in human or non-human animals.

Suitable non-human animals are non-human mammals.

The present invention further provides a compound of the general formula (I), or a pharmaceutically acceptable ester thereof; or pharmaceutically acceptable salt thereof, for use in the treatment of hyperglycaemia in human or non-human animals.

A compound of the general formula (I) or a pharmaceutically acceptable ester thereof; or a pharmaceutically acceptable salt thereof may be administered per se or, preferably, as a pharmaceutical composition also comprising a pharmaceutically acceptable carrier.

Accordingly, the present invention also provides a pharmaceutical composition comprising a compound of the general formula (I) or a pharmaceutically acceptable ester thereof; or a pharmaceutically acceptable salt thereof with a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment of hyperglycaemia in a human or non-human animal which method comprises administering an effective, non-toxic, amount of a compound of the general formula (I) or a pharmaceutically acceptable ester thereof; or a pharmaceutically acceptable salt thereof to a hyperglycaemic human or non-human animal.

The present invention further provides a method for the treatment of obesity in a human or non-human animal, which method comprises administering an effective, non-toxic, amount of a compound of the general formula (I) or a pharmaceutically acceptable ester thereof; or a pharmaceutically acceptable salt thereof to an obese human or non-human animal.

Conveniently, the active ingredient may be administered as a pharmaceutical composition hereinbefore defined, and this forms a particular aspect of the present invention.

In treating hyperglycaemic or obese humans the compound of the general formula (I) or pharmaceutically acceptable ester thereof; or a pharmaceutically acceptable salt thereof may be taken in doses, such as those described above, one to six times a day in a manner such that the total daily dose for a 70 kg adult will generally be in the range of from 0.1 to 6000 mg, and more usually about 1 to 1500 mg.

In treating hyperglycaemic or obese non-human animals, especially dogs, the active ingredient may be adminstered by mouth, usually once or twice a day and in an amount in the range of from about 0.025 mg/kg to 25 mg/kg, for example 0.1 mg/kg to 20 mg/kg.

The present invention further provides the use of a compound of formula (I), or a pharmaceutically acceptable ester thereof; or a pharmaceutically acceptable salt thereof, for the manufacture of a medicament for the treatment of obesity or hyperglycaemia.

In a further aspect the present invention also provides a method for increasing weight gain and/or improving the feed utilisation efficiency and/or increasing lean body mass and/or decreasing birth mortality rate and increasing the post-natal survival rate; of livestock, which method comprises the administration to livestock of an effective non-toxic amount of a compound of formula (I) or a veterinarily acceptable ester thereof; or a veterinarily acceptable salt thereof.

A suitable method is for increasing weight gain and/or improving the feed utilisation efficiency and/or increasing the lean body mass of livestock.

Whilst the compounds of formula (I) and the veterinarily acceptable esters thereof; or veterinarily acceptable salts thereof may be administered to any livestock in the abovementioned method, they are particularly suitable for increasing the weight gain and/or feed utilisation efficiency and/or lean body mass and/or decreasing birth mortality rate and increasing the post-natal survival rate; in poultry, especially turkeys and chickens, cattle, pigs and sheep.

In the preceding method the compounds of formula (I) or veterinarily acceptable esters thereof; or veterinarily acceptable salts thereof will normally be administered orally although non-oral modes of administration, for example injection or implantation, are also envisaged. Suitably the compounds are administered in the feed-stuff or drinking water provided for the livestock. Conveniently these are administered in the feed-stuff at from $10^{-3}$ ppm-500 ppm of total daily fed intake, more usually 0.01 ppm to 250 ppm, suitably less than 100 ppm.

The particular formulations used will of course depend upon the mode of administration but will be those used conventionally in the mode of administration chosen.

For administration in feed-stuff the drugs are conveniently formulated as a premix in association with a suitable carrier.

Accordingly, the present invention also provides a veterinarily acceptable premix formulation comprising a compound of formula (I) or a veterinarily acceptable ester thereof; or a veterinarily acceptable salt thereof in association with a veterinarily acceptable carrier therefore.

Suitable carriers are inert conventional agents such as powdered starch. Other conventional feed-stuff premix carriers may also be employed.

No toxicological effects are indicated when a compound of formula (I) or a pharmaceutically acceptable salt thereof is administered in any of the abovementioned dosage ranges.

The following Examples illustrate the invention but do not limit it in any way.

EXAMPLE 1

4-[4-[2-[(3-Chloro-β-hydroxyphenethyl)amino]propyl]-phenoxy]-3-hydroxy-1H-pyrrole-2,5-dione, hemihydrate A solution of 2-(3-chlorophenyl)-2-hydroxyethylamine (0.6 g) and the sodium salt of 4-[4-acetonylphenoxy]-3-hydroxy-1H-pyrrole-2,5-dione(1.0 g) in ethanol, was treated with sodium cyanoborohydride (0.25 g) and stirred at ambient temperature for 18 h. The solvent was evaporated in vacuo, the residue shaken with ethyl acetate and water and filtered. The insoluble material was washed with acetone and crystallised from methanol: water (95:5) to give 4-[4-[2-[(3-chloro-β-hydroxyphenethyl)amino]propyl]phenoxy]-3-hydroxy-1H-pyrrole-2,5-dione, hemihydrate, (0.55 g), as a (27:73)mixture of diastereoisomers.

$^1$H NMR (DMSO-$d_6$)ppm:
1.0 (3H,dd);2.4(1H,m);3.0–3.3(4H,m);5.0(1H,m), 6.8(2H,d);7.0(2H,d);7.4(4H,m);8.0–9.5(1H, very broad exch.$D_2O$);9.1(2H, broad s,exch.$D_2O$).

EXAMPLE 2

4-[4-[2-[(β,4-Dihydroxyphenethyl)amino]propyl]-phenoxy]-3-hydroxy-1H-pyrrole-2,5-dione,hydrate A solution of 2-(4-benzyloxyphenyl)-2-hydroxyethylamine (0.48 g) and 4-[4-acetonylphenoxy]-3-hydroxy-1H-pyrrole-2,5-dione, sodium salt (0.56 g) in methanol was treated with sodium cyanoborohydride (0.15 g) and stirred at ambient temperature for 18 h. The solvent was evaporated in vacuo, the residue shaken with ethyl acetate and water and filtered. The residue was washed with acetone, dissolved in glacial acetic acid and hydrogenated at ambient temperature and pressure over 10% palladium on charcoal. After filtration and evaporation of the solvent in vacuo the residue was crystallised from acetonitrile:water (95:5) to give 4-[4-[2-[(β,4-dihydroxyphenethyl)amino]propyl]-phenoxy]-3-hydroxy-l1H-pyrrole-2,5-dione,hydrate, (0.2 g), as a (10:90) mixture of diastereoisomers.

$^1$H NMR (DMSO-$d_6$)ppm:
1.0 (3H,d); 2.5(1H,m);3.0(3H,m);3.25(1H,m);3.25–3.5(3H, broad exch.$D_2O$); 4.75(1H,m); 5.25–6.3(1H, very broad, exch.-$D_2O$); 6.75(4H,dd); 7.1(2H,d); 7.2(2H,d);7.5–8.75(1H, very broad exch $D_2O$); 8.9(1H,s exch.$D_2O$); 9.4(1H, broad exch.$D_2O$).

EXAMPLE 3

2-[4-[2-[(3-Chloro-β-hydroxyphenethyl)amino]propyl]-phenoxymethyl]-5-hydroxy-4H-pyran-4-one.

A solution of 2-(4-acetonylphenoxymethyl)-5-hydroxy-4H-pyran-4-one (0.7 g) and 2-(3-chlorophenyl)-2-hydroxyethylamine carbonate 0.52 g in benzene was heated under reflux for 2.5 h using a Dean and Stark head. The reaction mixture was allowed to cool and the solvent removed in vacuo. The residue was taken up in methanol, treated with sodium cyanoborohydride (0.2 g) and stirred at ambient temperature for 18 h. The solvent was evaporated under reduced pressure, the residue dissolved in ethyl acetate, washed with water (2×50 ml), brine(1×50 ml) and dried (magnesium sulphate). After filtration and evaporation of solvent the residue was purified by column chromatography on silica using methanol:chloroform (3:97) as eluent, followed by crystallisation from acetone to give 2-[4-[2-[(3-chloro-β-hydroxyphenethyl)amino]propyl]-phenoxymethyl]-5-hydroxy-4H-pyran-4-one, (0.1 g), as a (35:65) mixture of diastereoisomers.

$^1$H NMR(DMSO-$d_6$)ppm:
0.9(3H,d);2.3–2.8(5H,m); 3.0–4.2(1H, very broad, exch. $D_2O$; 4.6(1H,m); 4.75–6.25(2H, very broad, exch.-$D_2O$); 4.9(2H,s); 6.5(1H,s); 6.8(2H,m); 7.1(2H,m); 7.3(4H,m) 8.1(1H,s).

EXAMPLE 4

5-[4-[2-[(β-4-Dihydroxyphenethyl)amino]propyl]benzyl]thiazolidine-2,4-dione.

A mixture of the sodium salt of octopamine (0.35 g) and 5-(4-acetonylbenzyl)thiazolidine-2,4-dione (0.52 g)

in methanol was treated with sodium cyanoborohydride (0.15 g) and stirred for 18 h at ambient temperature. The solvent was removed in vacuo and the residue purified by column chromotography using acetone as eluent to give 5-[4-[2-[($\beta$-4-dihydroxyphenethyl)amino]propyl]-benzyl] thiazolidine-2,4-dione, (0.3 g), as a (45:55) mixture of diastereoisomers.

'H NMR (DMSOd$_6$) ppm:

1.0(3H,d); 2.5(1H,m); 2.8(4H,m); 3.2(1H,m); 3.3(1H,m);4.5(1H,m); 4.7(1H,m); 5.0-7.5(4H, very broad exch.D$_2$O); 6.4(2H,d); 7.2(6H,m).

EXAMPLE 5

5-[4-[2-[(3-Chloro-$\beta$-hydroxyphenethyl)amino]propyl]-benzyl]thiazolidine-2,4-dione,hemihydrate.

A mixture of 5-(4-acetonylbenzyl)thiazolidine-2,4-dione (0.9 g) and 2-(3-chlorophenyl)-2-hydroxyethylamine (0.6 g) in dry benzene (80 ml) was heated under reflux, with azeotropic removal of water, for 1 h. The solvent was evaporated, and the residue dissolved in methanol (80 ml) and treated with sodium cyanoborohydride (0.5 g). After 16 h at ambient temperature the methanol was evaporated and the residue partitioned between ethyl acetate and water. The organic phase was washed with water, dried (MgSO$_4$) and evaporated to a foam which was chromatographed on silica gel. Elution with methanol in chloroform (6:94) gave 5-[4-[2-[(3-chloro-$\beta$-hydroxyphenethyl)amino]propyl]benzyl]thiazolidine-2, 4-dione,hemihydrate as a white crystalline solid (ethyl acetate), mp. 149°-160° C. as a 54:46 mixture of diastereoisomers.

'H NMR (DMSO-d$_6$)ppm:

0.97(3H,d); 2.72-3.08(5H,m); 3.15-3.90 (2H,m+4H, broad exch. D$_2$O); 4.68(2H,m); 7.13(4H,m); 7.27-7.53(4H,m).

EXAMPLE 6

5-[4-[2-[(4-Amino-3,5-dichloro-$\beta$-hydroxyphenethyl)amino]propyl]benzyl]thiazolidine-2,4-dione.

5-[4-[2-[(4-Amino-3,5-dichloro-$\beta$-hydroxyphenethyl)amino]propyl]benzyl]thiazolidine-2,4-dione was prepared as a 46:54 mixture of diastereoisomers, mp. 195°-201° C., from 2-(4-amino-3,5-dichlorophenyl)-2-hydroxy ethylamine and 5-(4-acetonylbenzyl)thiazolidine-2,4-dione in an analogous manner to that described in Example 5

'H NMR (DMSO-d$_6$)ppm:

0.95(3H,d); 2.68-3.08(5H,m); 3.20-4.30(2H,m+3H, broad, exch.D$_2$O); 4.56(2H,m); 5.38(2H,s, exch.D$_2$O); 7.13(4H,m); 7.21(2H,s).

EXAMPLE 7

5-[4-[2-[(3-Chloro-$\beta$-hydroxyphenethyl)amino]propyl]-phenoxymethyl]tetrazole.

A mixture of 4-[2-[(3-chloro-$\beta$-hydroxyphenethyl)amino]phenoxyacetonitrile (0.5 g), sodium azide (96 mg), and ammonium chloride (80 mg) in dry dimethylformamide was heated at 100° C. for 6 h. The reaction was cooled and the solvent evaporated in vacuo. The residue was chromatographed on silica using methanol-chloroform (5:95) as eluent until starting materials had eluted; the solvent was then changed to methanol-chloroform (20:80) to give 5-[4-[2-[(3-chloro-$\beta$-hydroxyphenethyl)amino]propyl]phenoxymethyl]tetrazole, (0.45 g) as a (46:54) mixture of diastereoisomers.

'H NMR (DMSO-d$_6$) ppm:

1.1(3H,d); 2.6(1H,m); 3.0-3.4(4H,m); 4.5-6.5(3H, very broad exch.D$_2$O); 4.9(1H,m); 5.2(2H,s); 6.9(2H,d); 7.15(2H,m); 7.4(4H,m)

EXAMPLE 8

5-[4-[2-[(3-Chloro-$\beta$-hydroxyphenethyl)amino]propyl]-phenyl]tetrazole.

A mixture of 2-(3-chlorophenyl)-2-hydroxyethylamine carbonate 1.1 g) and 5-(4-acetonylphenyl)tetrazole in benzene was heated under reflux for 3 h using a Dean and Stark head. The reaction mixture was cooled and the solvent evaporated in vacuo. The residue was dissolved in methanol, and treated with sodium cyanoborohydride (0.5 g) and stirred at ambient temperature for 24 h. The solvent was evaporated in vacuo, the residue treated with water, evaporated to dryness, and purified by column chromatography on silica using methanol-chloroform (15:85) as eluent to give 5-[4-[2-(3-chloro-$\beta$-hydroxyphenethyl)amino]propyl]phenyl]tetrazole, (0.57 g), as a 51:49 mixture of diastereoisomers.

$^1$H NMR(DMSO-d$_6$) ppm:

1.1(3H,d); 2.4-2.9(1H,m); 2.9-3.7(4H,m); 5.0(1H,m); 7.0(3H broad s,exch.D$_2$O); 7.35(6H,m); 8.0(2H,d).

EXAMPLE 9

5-[4-[2-[(3-Chloro-$\beta$-hydroxyphenethyl)amino]propyl]-phenyl]-3-hydroxyisoxazole.

A solution of 2-(3-chlorophenyl)-2-hydroxyethylamine (0.5 g) and 5-(4-acetonylphenyl)-3-hydroxyisoxazole (0.5 g) in benzene was heated under reflux for 3 h, using a Dean and Stark head, cooled and the solvent evaporated in vacuo. The residue was dissolved in methanol, treated with sodium cyanoborohydride (0.175 g) at ambient temperature for 16 h and the solvent removed in vacuo. The residue was treated with water, filtered, washed with a little acetone and recrystallised from acetonitrile to give 5-[4-[2-(3-chloro-$\beta$-hydroxyphenethyl) amino]propyl]phenyl]-3-hydroxyisoxazole, (0.12 g), as a (62:38) mixture of diastereoisomers.

'H NMR(DMSO-d$_6$) ppm:

1.0(3H,d); 2.6-3.0(5H,m); 4.7(1H,m); 4.75-6.25(3H, very broad exch.D$_2$O); 6.4(1H,s); 7.3(6H,m); 7.7(2H,m).

EXAMPLE 10

2-[4-[2-[(3-Chloro-$\beta$-hydroxyphenethyl)amino]propyl]-phenoxymethyl]-5-hydroxy-1H-pyrid-4-one dihydrochloride A solution of 2-[4-[2-[(3-chloro-$\beta$-hydroxyphenethyl)amino]propyl] phenoxymethyl]-5-benzyloxy-4H-pyran-4-one (2 g) in methanol (10 ml) was treated with ammonia solution, SG 0.88, (5 ml) and heated to 120° C. in a sealed vessel for 18 hours. After evaporation of the solvent in vacuo the residue was crystallised from ethanol to give 2-[4-[2-[(3-chloro-$\beta$-hydroxyphenethyl)amino]-propyl]phenoxymethyl]-5-benzyloxy-1H-pyrid-4-one (1.6 g , which was dissolved in methanol and the solution acidified with 2M hydrochloric acid solution to pH 1.5-2.0 and hydrogenated at room temperature and pressure over 10% palladium on charcoal. After filtration and evaporation of the solvent in vacuo the residue was treated with 1.2M sodium hydrogen carbonate solution (5 ml) and extracted with ethyl acetate (3×50 ml), dried (magnesium sulphate), filtered and evaporated under reduced pressure to give an oil. This was dissolved in methanol and treated with methanolic hydrogen chloride. Evaporation in vacuo gave 2-[4-[2-[(3-chloro-β-hydroxyphenethyl)amino]propyl]-phenoxymethyl]-5-hydroxy-1H-pyrid-4-one dihydrochloride as a (37:63) mixture of diastereoisomers.

¹H NMR (DMSO-d₆) ppm:

1.1 (3H,d); 2.65 (1H,m); 3.25 (4H,m); 5.1 (1H,d); 5.25 (2H,s); 6.4 (1H, broad s, exchange with D₂O); 7.0 (2H,d); 7.2 (2H,d); 7.4 (5H,m); 8.1 (1H,s); 8.8 (1H, broad s, exchange with D₂O); 9.5 (1H, broad s, exchange with D₂O); 14.75–12.25 (1H, very broad, exchange with D₂O).

EXAMPLE 11

2-[4-[2-[(3-Chloro-β-hydroxyphenethyl)amino]propyl]-phenoxymethyl]-5-hydroxy-1-methyl-1H-pyrid-4-one A suspension of 2-[4-[2 [(3-chloro-β-hydroxyphenethyl)amino]propyl]phenoxymethyl]-5-benzyloxy-4H-pyran-4-one (1.0 g) in 33% ethanolic methylamine solution (15 ml), was heated to 120° in a sealed vessel for 18 hours. The solvent was evaporated in vacuo and the residue purified by column chromatography on silica using chloroform, then 10% methanol:chloroform as eluent. The resulting gum was dissolved in methanol and 2M hydrochloric acid was added dropwise to bring the pH to 1.5–2.0. The solution was then hydrogenated at room temperature and pressure over 10% palladium on charcoal. After filtration and evaporation of solvent in vacuo the residue was treated with 1.2M sodium hydrogen carbonate solution (5 ml), and extracted with ethyl acetate (3×50 ml), and dried (MgSO₄). After filtration and evaporation of solvent the residue was triturated with acetone to give 2-[4-[2-[(3-chloro-β-hydroxyphenethyl)amino]propyl]phenoxymethyl]-5-hydroxy-1-methyl-1H-pyrid-4-one (0.7 g) as a (40:60) mixture of diastereoisomers.

¹H NMR (DMSO-d₆) ppm:

0.9 (3H,d); 2.3–2.8 (5H,m); 3.6 (3H,s); 4.6 (1H,t); 5.0 (5H, broad s, partially exchanged with D₂O to 2H,s); 6.4 (1H,s); 6.9 (2H,m); 7.1 (2H,m); 7.3 (4H,m); 7.5 (1H,s).

EXAMPLE 12

2-[4-[2-[(β,4-Dihydroxyphenethyl)amino]propyl]-phenoxymethyl]-5-hydroxy-4H-pyran-4-one A mixture of the sodium salt of octopamine (0.65 g), and 2-(4-acetonylphenoxymethyl)-5-hydroxy-4H-pyran-4-one (1.0 g) in methanol was treated with sodium cyanoborohydride (0.3 g) and stirred at ambient temperature for 18 hours. The solvent was evaporated in vacuo. The residue was suspended in acetone and filtered, washed with acetone and then purified by column chromatography on silica using 5% methanol:chloroform as eluent-increasing to 15% methanol:chloroform after elution of fast-running impurities. This gave 2-[4-[2-[(β,4-dihydroxyphenethyl)amino]propyl]-phenoxymethyl]-5-hydroxy-4H-pyran-4-one(0.4 g) as a (50:50) mixture of diastereoisomers.

¹H NMR (DMSO-d₆) ppm:

0.9 (3H,d); 2.3–3.0 (5H,m); 4.5 (1H,m); 4.9 (2H,s); 6.5 (1H,s); 6.6–7.3 (8H,m); (1H,s); 8.3–3.5 (4H, very broad, exchanged with D₂O).

EXAMPLE 13

2-[4-[2-[(4-Amino-3,5-dichloro-β-hydroxyphenethyl)amino]propyl]phenoxymethyl]-5-hydroxy-4H-pyran-4-one A solution of 2-[4-acetonylphenoxymethyl]-5-hydroxy-4H-pyran-4-one (1.0 g) and 2-(4-amino-3,5-dichlorophenyl)-2-hydroxyethylamine (0.75 g) in benzene, was heated to reflux for 3 hours under a Dean and Stark head. After cooling, the solvent was removed in vacuo, the residue dissolved in methanol, treated with sodium cyanoborohydride (0.25 g) and then stirred at ambient temperature for 18 hours. The solvent was evaporated under reduced pressure and the residue taken up in ethyl acetate and washed with water (2×50ml), brine (1×50 ml) and dried (MgSO₄). After filtration and evaporation of solvent the residue was purified by column chromatography on silica using 3% methanol:chloroform as eluent to give 2-[4-[2-[(4-amino-3,5-dichloro-β-hydroxyphenethyl)amino]-propyl]phenoxymethyl]-5-hydroxy-4H-pyran-4-one as a (40:60) mixture of diastereoisomers.

¹H NMR (DMSO-d₆) ppm:

0.9 (3H,d); 2.3–2.8 (5H,m); 4.4 (1H,m); 4.9 (2H,s); 5.3 (2H,s, exchanged with D₂O); 5.8–4.6 (3H, very broad, exchanged with D₂O); 6.5 (1H,s) 6.8–7.2 (6H,m); 8.1 (1H,s).

EXAMPLE 14

4-[4-[2-[(4-Amino-3,5-dichloro-β-hydroxyphenethyl)amino]propyl]phenoxy-3-hydroxy-1H-pyrrole-2,5-dione, hemihydrate A solution of the sodium salt of 4-(4-acetonylphenoxy)-3-hydroxy-1H-pyrrole-2,5-dione (1.41 g) and 2-(4-amino-3,5-dichlorophenyl)-2-hydroxy ethylamine (1.0 g) in methanol was treated with sodium cyanoborohydride (0.35 g) and stirred at ambient temperature for 18 hours. The solvent was removed in vacuo, the residue dissolved in acetone and purified by column chromatography on silica using acetone as eluent followed by methanol after the elution of fast-running impurities. The solid obtained was washed with acetone and filtered to give 4-[4-[2-[(4-amino-3,5-dichloro-β-hydroxyphenethyl)amino]propyl]phenoxy]-3-hydroxy-1H-pyrrole-2,5-dione hemihydrate as a (34:66) mixture of diastereoisomers.

¹H NMR (DMSO-d₆) ppm:

0.9 (3H,m); 2.9–3.5 (5H,m); 4.8 (1H,m); 5.5 (2H,s, exchanged with D₂O); 6.5–5.2 (1H, broad, exchanged with D₂O); 6.8 (2H,d); 7.0 (2H,d); 7.3 (2H,s); 9.1 (1H,s, exchanged with D₂O); 9.5–8 (2H, very broad, exchanged with D₂O).

EXAMPLE 15

5-[4-[2-[(3-Chloro-β-hydroxyphenethyl)amino]propyl]-phenoxymethyl]3-hydroxyisoxazole.

A solution of 5-(4-acetonylphenoxymethyl)-3-hydroxyisoxazole (0.6 g and 3-chloro-β-hydroxy phenethylamine (0.42 g) in benzene, was heated under reflux for 3 h using a Dean and Stark head.

The reaction was cooled and the solvent removed in vacuo. The residue was dissolved in methanol, treated with sodium cyanoborohydride (0.2 g) and stirred at room temperature for 18 h. The solvent was removed in vacuo, the residue triturated with ethyl acetate, filtered and chromatographed on silica. Elution with chloroform:methanol (95:5) gave 5-[4-[2-[(3-chloro-β-hydroxyphenethyl)amino]propyl]phenoxymethyl]-3-hydroxyisoxazole (0.3 g) as a 55:45 mixture of diastereoisomers.

¹H NMR (DMSO-d₆) ppm:

0.9 (3H,d); 2.3-2.9 (5H,m); 3.0-4.0 (2H, broad, exchanges with D₂O); 4.6 (1H,m); 4.8(2H,s); 5.0-6.4 (1H, very broad, exchanges with D₂O); 5.4 (1H,s); 6.8 (2H,m); 7.1 (2H,m); 7.2-7.5 (4H,m).

EXAMPLE 16

2-[4-[2-[(3-Chloro-β-hydroxyphenethyl)amino]propyl]phenoxymethyl]-5-hydroxy-6-dimethylaminomethyl-4H-pyran-4-one.

A solution of 2-[4-[2-[(3-chloro-β-hydroxyphenethyl)amino]propyl]phenoxymethyl]-5-hydroxy-4H-pyran-4-one 0.8 g) in ethanol, was added to a mixture of dimethylamine (0.28 ml of a 33% solution, in ethanol) and formaldehyde (0.175 ml of a 37% aq. solution) in ethanol:water (95:5), (50 ml), at room temperature and allowed to stand for 1h. The solvent was evaporated in vacuo, the residue was partitioned between ethyl acetate and water separated and the organic extracts dried (magnesium sulphate), filtered and evaporated to an oil which was chromatographed on silica. Elution with chloroform: methanol (95:5) gave 2-[4-[2-[(3-chloro-β-hydroxyphenethyl)amino]propyl]phenoxymethyl]-5-hydroxy-6-dimethylaminomethyl-4H-pyran-4-one (0.4 g) as a 49:51 mixture of diastereoisomers.

¹H NMR (DMSO-d₆) ppm:

0.9 (3H,d); 2.2 (6H,s); 2.25 (5H,m); 3.5 (2H,s); 3.8-6.2 (3H, very broad, exchanges with D₂O); 4.6 (1H,m); 5.0(2H,s); 6.5 (1H,s); 6.9 (2H,m); 7.1 (2H, m); 7.2-7.5 (4H,m).

EXAMPLE 17

Ethyl 4-hydroxy-1-[4-[2-[(3-chloro-β-hydroxyphenethyl)amino]propyl]phenyl]-2-oxo-3-pyrroline-3-carboxylate, sodium salt.

Ethyl [N[4-[2-[(3-chloro-β-hydroxyphenethyl)amino]-propyl]phenyl]-N-carbomethoxymethyl]-malonamide (0.306 g, 0.64 mmol) was added as a 5 ml ethanolic solution to sodium ethoxide (0.64 mmol) in ethanol (10 ml) and the solution stirred for 4 h until the starting material had been consumed (t.l.c.). The solution was then evaporated in vacuo to provide the sodium salt of ethyl 4-hydroxy-1-[4-[2-[(3-chloro-β-hydroxyphenethyl)-amino]propyl]phenyl]-2-oxo- 3-pyrroline-3-carboxylate (0.304 g, 100%) as a yellow solid, as a 1:1 mixture of diastereoisomers, m.p.>300° C.

¹H NMR DMSO-d₆) ppm:

0.9 (3H,d ; 1.2 (3H,t ; 1.6 (1H,br s ; 2.25-3.8 (5H,m); 3.7 (2H,s); 4.05 (2H,q); 4.6 (1H,t); 5.35 (1H,br s); 7.0 (2H,d.d.); 7.3 (4H,m); 7.6 (2H, d.d.).

EXAMPLE 18

3-Chloro-α-[[[2-[4-(3-pyridylmethyloxy)phenyl]-1-methylethyl]amino]methyl]benzenemethanol.

A mixture of 1-[4-(3-pyridylmethyloxy)phenyl]propan-2-one (7.2 g) and 2-hydroxy-2-(3-chlorophenyl)ethanamine (5.1 g) was boiled under reflux with azeotropic removal of water until the reaction was complete. The solvent was evaporated, the residue dissolved in methanol (150 ml), cooled in an ice-bath and treated with sodium borohydride (5 g). After stirring for 1 hour the methanol was evaporated and the residue partitioned between ethyl acetate and water. The organic phase was washed with water, dried and evaporated to give an oil which was chromatographed on Kieselgel 60. Elution with 3% methanol in chloroform gave a yellow oil (6.4 g). Bulb to bulb distillation of this oil gave 3-chloro-β-[[[2-[4-(3-pyridylmethyloxy)phenyl]-1-methylethyl]amino]methyl]benzenemethanol b.p. 120°-130° C./0.4 mm, as a 1:1 mixture of diastereoisomers.

¹HNMR (CDCl₃) ppm:

1 09 (d,3H), 2.43-3.10 (m,5H+2H replaceable by D₂O), 4.60 (m,1H), 5.08 (s,2H), 6.80-6.43 (m,9H), 7.80 (d,1H), 8.49-8.74 (m,2H).

EXAMPLE 19

3-Chloro-α-[[[2-[4-(2-pyridylmethyloxyphenyl]-1-methylethyl]amino]methyl]benzenemethanol, hemihydrate A mixture of 1-[4-(2-pyridylmethyloxy)phenyl]propan-2-one(7.6 g) and 2-hydroxy-2-(3-chlorophenyl)ethanamine (5.4 g) in benzene (150 ml) was boiled under reflux with azeotropic removal of water until the reaction was complete. The solvent was evaporated and the residue dissolved in methanol (150 ml), cooled in an ice bath and treated with sodium borohydride (5 g). After stirring for 1 hour the methanol was evaporated and the residue partitioned between ethyl acetate and water. The organic phase was washed with water, dried and evaporated to give an oil which was chromatographed on Kieselgel 60. Elution with 3% methanol in chloroform gave 3-chloro-α-[[[2-[4-(2-pyridylmethyloxyphenyl]-1-methylethyl]amino]methyl]benzenemethanol, hemihydrate which crystallised from ethyl acetate as an 80:20 mixture of diastereoisomers, m.p. 123.5°-127° C.

¹H NMR (CDCl₃+D₂O) ppm:

1.07 (d,3H), 2.46-3.09 (m,5H), 4.53-4.74 (m,1H), 4.69 (s, HOD), 5.21 (s,2H), 6.82-7.89 (m,11H), 8.63 (d,1H).

¹H NMR δ (DMSO-hd 6):

1.00 (d,3H); 2.50-3.60 (m,5H); 5.05 (m,1H); 5.43 (s,2H); 5.7-6.6 (broad, 2H replaceable by D₂O); 6.90-7.18 (q,4H); 7.23-7.55 (m,4H); 8.04 (d,2H); 8.30-9.00 (broad, 2H replaceable by D₂O+d,2H).

EXAMPLE 20

3-chloro-α-[[[2-[4-[4-pyridylmethyloxy)phenyl]-1-methylethyl]amino]methyl]benzenemethanol A mixture of 1-[4-(4-pyridylmethyloxy)phenyl)propan-2-one (2.5 g) and 2-hydroxy-2-(3-chlorophenyl)ethanamine (1.78 g) in benzene (100 ml) was boiled under reflux with azeotropic removal of water until the reaction was complete. The solvent was evaporated, the residue dissolved in methanol (150 ml), cooled in an ice bath and treated with sodium borohydride (1.0 g). After stirring for 1 hour the methanol was evaporated, the residue partitioned between ethyl acetate and water, the washed organic phase dried and evaporated to give an oil which was chromatographed on Kieselgel 60. Elution with 4% methanol in chloroform gave 3-chloro-α-[[[2-[4-[4-pyridylmethyloxy)phenyl]-1-methylethyl]amino]methyl]benzenemethanol m.p. 85°-110° C. (ethylacetate-ether) as a 45:55 mixture of diastereoisomers.

¹H NMR (CDCl₃) ppm:

1.04 (d,3H); 2.4-3.05 (m,5H+2H replaceable by D₂O), 4.55 (m,1H), 5.07 (s,2H), 6.75-7.45 (m,1 OH), 8.51-8.68 (m,2H).

Repetition of the above experiment but treatment of the chromatographed oil with gaseous hydrogen bromide gave 3-chloro-α-[[[2-[4-[4-pyridylmethyloxy)-phenyl]-1-methylethyl]amino]methyl]benzenemethanol, dihydrobromide. m.p. 132°–135° C. (isopropanol-methanol) as a 93:7 mixture of diastereoisomers.

EXAMPLE 21

3-Chloro-α-[[[2-[4-(2-piperidinylmethyloxy)phenyl]-1-methylethyl]amino]methyl]benzenemethanol, dihydrochloride 3-Chloro-α-[[[2-[4-(2-pyridylmethyloxy)phenyl]-1-methylethyl]amino]methyl]benzene methanol, (2.5 g) in ethanol (40 ml) and 2M hydrochloride acid (40 ml) was hydrogenated at atmospheric pressure in the presence of platinum oxide. The reaction mixture was filtered, the filtrate neutralised with 2M sodium hydroxide solution, extracted with ethyl acetate and dried. Evaporation of the solvent gave an oil which was treated with ethereal hydrogen chloride to give 3-chloro-α-[[[2-[4-(2-piperidinylmethyloxy)phenyl]-1-methylethyl]amino]methyl] benzenemethanol, dihydrochloride m.p. 181°–198C. (methanol-ether), as a 95:5 mixture of diastereoisomers.

$^1$H NMR (DMSO-$d_6$) ppm: 1.13 (d,3H), 1.3–2.0 (m,6H) 2.5–3.6 (m,8H + 1H, replaceable by $D_2O$), 4.13 (d,2H), 5.18 (m,1H), 6.4 (broad, 1H, replaceable by $D_2O$), 6.87–7.67 (m,8H), 8.5–10.1 (broad, 3H, replaceable by $D_2O$).

EXAMPLE 22

3-Chloro-α-[[[2-[4-(3-piperidinylmethyloxy)phenyl]-1-methylethyl]amino]methyl]benzenemethanol, dihydrochloride.

3-Chloro-α-[[[2-[4-(3-piperidinylmethyloxy)phenyl]-1-methylethyl]amino]methyl]benzenemethanol, dihydrochloride was prepared (as a 36:64 mixture of diastereoisomers, m.p. 94°–103° C.) in an analogous manner to the compound described in Example 21.

$^1$H NMR (DMSO-$d_6$) ppm:
1.15 (d,3H), 1.35–2.15 (m,6H), 2.55–3.70 (m,10H), 3.88 (m,2H), 5.20 (m,1H), 6.80–7.65 (m,8H), 8.6–10.2 (broad, 3H replaceable by $D_2O$).

EXAMPLE 23

3-Chloro-α-[[[2-[4-(4-piperidinylmethyloxy)phenyl]-1-methylethyl]amino]methyl]benzenemethanol, 3-Chloro-α-[[[2-[4-(4-piperidinylmethyloxy)phenyl]-1-methylethyl]amino]methyl]benzenemethanol, dihydrochloride was prepared (as a 91;9 mixture of diastereoisomers, m.p. 99°–105° C.) in an analogous manner to the compound described in Example 21.

$^1$H NMR (DMSO-$d_6$) ppm:
1.18 (d,3H , 1.3–2.3 (m,6H), 2.55–3.6 (m,8H + 2H replaceable by $D_2O$) 3.88 (d,2H), 5.2 (m,1H), 6.78–7.6 (m,8H), 8.7–10.05 (broad 3H replaceable by $D_2O$).

EXAMPLE 24

3-Chloro-α-[[[2-[4-((4,5-dihydro-1H-2-imidazolyl)methyloxy)phenyl]-1-methylethyl]amino]methyl]benzenemethanol, dihydrochloride.

1,2-Diaminoethane (0.44 g) in dry toluene (50 ml) was added under nitrogen to a stirred 25% solution of triisobutylaluminium (6.5 mmole) in hexane at <10° C. The solution was allowed to attain ambient temperature and a solution of methyl 4-[2-[(3-chloro-β-hydroxyphenethyl) amino]propyl]phenoxyacetate (generated from 2 g of the hydrobromide salt) in toluene (20 ml) added and the mixture heated under reflux for 7 h. The reaction mixture was cooled and decomposed below −5° C. with a mixture of water (2 ml), dichloromethane (6 ml) and methanol (6 ml). This mixture was boiled for 0.5 h, dried (magnesium sulphate) filtered and evaporated. The resulting oil was taken up in ethyl acetate, dried, filtered and evaporated. The resulting oil was treated with ethereal hydrogen chloride 3-chloro-α-[[[2-[4-((4,5-dihydro-1H-2-imidazolyl)methyloxy)-phenyl]-1-methylethyl]amino]methyl] benzenemethanol, dihydrochloride m.p. 252°–256° C. (methanol-ether) as a >95:5 mixture of diastereoisomers.

$^1$H NMR (DMSO-$d_6$) ppm:
1.08 (d,3H), 2.4–3.65 (m,5H + 1H replaceable by $D_2O$), 3.77 (s,4H), 4.95–5.3 (s+m,3H), 6.8–7.65 (m,8H + 1H replaceable by $D_2O$), 8.2–10.5 (m,3H replaceable by $D_2O$).

EXAMPLE 25

α-[[[2-[4-(Pyridylmethyloxy)phenyl-1-methylethyl]amino]benzenemethanol hydrobromide.

α-[[[2-[4-(Pyridylmethyloxy)phenyl-1-methylethyl]amino]benzenemethanol, hydrobromide was prepared from 4-(4-pyridylmethyloxy)phenyl)propan-2-one and 2-hydroxy-2-phenylethanamine in an analogous manner to the compound described in Example 20. Treatment of an ethereal solution of the free base with gaseous hydrogen bromide gave the monohydrobromide salt, m.p. 120°–155° C. (ethylacetate-methanol) as a 70:30 mixture of diastereoisomers.

$^1$H NMR (DMSO-$d_6$) ppm:
1.06 (d,3H); 2.50–3.60 (m,5H + 1H replaceable by $D_2O$); 4.85–5.12 (m,1H + s,2H); 6.85–7.50 (m, 1 OH + 1H replaceable by $D_2O$); 8.45–8.70 (m,2H + 1H replaceable by $D_2O$).

EXAMPLE 26

3-Trifluoromethyl-α-[[[2-[4-(4-pyridylmethyloxy)phenyl]-1-methylethyl]amino]methyl]benzenemethanol.

3-Trifluoromethyl-α-[[[2-[4-(4-pyridylmethyloxy)-phenyl]-1-methylethyl]amino]methyl]benzenemethanol was prepared as a 56:44 mixture of diastereoisomers, m.p. 83°–90° C., from 4-(4-pyridylmethyloxy)phenyl]-propan-2-one and 2-hydroxy-2-(3-trifluoromethylphenyl)ethanamine in an analogous manner to the compound described in Example 20.

$^1$H NMR (CDCl$_3$) ppm.
1.06 (d,3H); 2.40–3.10 (m,5H + 2H replaceable by $D_2O$); 4.65 (m,1H); 5.07 (s,2H); 6.80–7.60 (m,1 OH); 8.55 (m,2H).

EXAMPLE 27

3-Chloro-α-[[[2-[4-(5-(2-oxotetrahydrooxazolyl)methyloxy)phenyl]-1-methylethyl]amino]methyl]benzenemethanol, hydrochloride.

A mixture of 4-(5-(2-oxo-tetrahydrooxazoly)methyloxy)phenyl propan-2-one (1.68g) and 2-hydroxy-2-(3-chlorophenyl)ethanamine (1.16 g) in benzene (80 ml) was heated under reflux, with azeotropic removal of water, for three hours. The solvent was evaporated and the residue dissolved in methanol (80 ml) and treated with sodium cyanoborohydride (1 g). After stirring for four hours the methanol was evaporated and the residue partitioned between ethyl acetate and water. The organic phase was washed with water, dried (MgSO$_4$) and evaporated to give an orange oil which was chromatographed on Kieselgel 60. Elution with 8% methanol in chloroform gave a foam which was dissolved in ethyl acetate and treated with gaseous hydrogen chloride to give 3-chloro-α-[[[2-[4-(5-(2-oxotetrahydrooxazolyl)methyloxy)phenyl]-1-methylethyl]amino]methyl]benzene- methanol, hydrochloride m.p. 148°-165° C., (ethylacetate/methanol) as a 68:32 mixture of diastereoisomers.

$^1$H NMR (DMSO-d$_6$) ppm:
1.10 (d,3H); 3.00-3.50 (m,7H+1H replaceable by D$_2$O); 4.10 (m,2H); 4.95 (m,2H); 6.25 (m,1H replaceable by D$_2$O); 6.90-7.70 (m,8H+1H replaceable by D$_2$O); 8.90 (m,1H replaceable by D$_2$O).

EXAMPLE 28

3-Chloro-α-[[[2-[4-(2-(4,5-dihydrothiazolyl)methyloxy)phenyl]-1-methylethyl]amino]methyl]benzenemethanol.

3-Chloro-α-[[[2-[4-(2-(4,5-dihydrothiazolyl)methyloxy)phenyl]-1-methylethyl]amino]methyl]benzenemethanol was prepared as a 13:87 mixture of diastereoisomers, mpt. 100°-107° C., from methyl 4-[2-[(3-chloro-α-hydroxyphenethyl)amino]propyl]phenoxyacetate and 2-aminoethane-thiol in an analogous manner to the compound described in Example 24.

$^1$H NMR (DMSO-d$_6$) ppm:
0.95 (d,3H); 2.50-3.00 (m,5H+1H replaceable by D$_2$O); 3.15-3.45 (t,2H); 4.05-4.35 (t,2H); 4.40-4.70 (m,1H); 4.90 (s,2H); 5.20-5.50 (m,1H replaceable by D$_2$O); 6.75-7.50 (m,8H).

EXAMPLE 29

3-Trifluoromethyl-α-[[[2-[4-(2-(5-oxomorpholinyl)methyloxy)phenyl]-1-methylethyl]amino]methyl]benzenemethanol.

A mixture of 4-(2-(5-oxomorpholinyl)methyloxy)phenylpropan-2-one (2.5 g) and 2-hydroxy-2-(3-trifluoromethylphenyl) ethanamine (1.95 g) in benzene (100 ml) was heated under reflux with azeotropic removal of water, for 2 hr. The solvent was evaporated and the residue dissolved in methanol (80 ml) and treated with sodium cyanoborohydride (1.5 g). After 2 hr. the methanol was evaporated and the residue partitioned between ethyl acetate and water. The organic phase was washed with water, dried (MgSO$_4$) and evaporated to an oil which was chromatographed on Kieselgel 60. Elution with 8% methanol in chloroform gave 3-trifluoromethyl-α-[[[2-[4-(2-(5-oxomorpholinyl)methyloxy)phenyl]-1-methylethyl]amino]methyl]benzenemethanol as a white crystalline solid, m.p. 63°-85° C., as a 33:67 mixture of diastereoisomers.

$^1$H NMR (CDCl$_3$) ppm:
1.10 (d,3H); 2.50-3.10 (m,5H+2H replaceable D$_2$O); 3.50 (d,2H); 3.90-4.35 (m,5H); 4,68 (m,1H); 6.70-7.25 (m,4H+1H replaceable by D$_2$O); 7.45-7.68 (m,4H).

EXAMPLE 30

3-Trifluoromethyl-α-[[[2-[4-((2-morpholinyl)methyloxy)phenyl]-1-methylethyl]amino]methyl]benzenemethanol, dihydrochloride.

A solution of 3-trifluoromethyl-α-[[[2-[4-(2-(5-oxomorpholinyl)methyloxy)phenyl]-1-methylethyl]amino]methyl]benzenemethanol (example 29) (1.05 g) in dry tetrahydrofuran (50 ml) was added, dropwise, under a nitrogen atmosphere to a stirred slurry of lithium aluminium hydride (0.5 g) in dry tetrahydrofuran (30 ml). The mixture was stirred at ambient temperature for 30 minutes, heated under reflux for 6 hr. cooled and treated with water (0.5 ml); 2N sodium hydroxide solution (0.5 ml), water (1.5 ml) and dichloromethane (30 ml). The mixture was filtered and the filtrate evaporated to a colourless oil which was purified by column chromatography on Kieselgel 60. Elution with 10% methanol in chloroform gave a colourless oil. An ethereal solution of the free base was treated with gaseous hydrogen chloride to give 3-trifluoromethyl-α-[[[2-[4-((2-morpholinyl)methyloxy)phenyl]-1-methylethyl]amino]methyl]benzenemethanol, dihydrochloride. 107°-113° C. as a 1:1 mixture of diastereoisomers.

$^1$H NMR (DMSO d$_6$) ppm:
1.10 (d,3H); 2.55-3.50 (m,9H+2H replaceable by D$_2$O); 3.70-4.25 (m,5H); 5.20 (m,1H); 6.40 (s,1H replaceable by D$_2$O); 6.80-7.25 (q,4H); 7.60-7.85 (m,4H); 9.85 (broad, 2H replaceable by D$_2$O).

EXAMPLE 31

3-Trifluoromethyl-α-[[[2-[4-(2-(4,5-dihydrothiazolyl)methyloxy)phenyl]-1-methylethyl]amino]methyl]benzenemethanol, dihydrochloride, hemihydrate.

3-Trifluoromethyl-α-[[[2-[4-(2-(4,5-dihydrothiazolyl)methyloxy)phenyl]-1-methylethyl]amino]methyl]benzenemethanol, dihydrochloride, hemihydrate, m.p. 127°-140° C. was prepared from methyl 4-[2-[(3-trifluoromethyl-β-hydroxyphenethyl)amino]propyl]phenoxyacetate and 2-aminoethanethiol in an analogous manner to the compound described in Example 24.

$^1$H NMR (DMSO-d$_6$) ppm:
1.15(d,3H); 2.85-3.80(m,9H); 4.95(s,2H); 5.20(m,1H); 6.50 (broad,1H replaceable by D$_2$O); 6.85-7.50(q,4H); 7.60-7.95(m,4H); 8.20(m,2H replaceable by D$_2$O); 8.90(broad, 1H replaceable by D$_2$O); 9.60(broad, 1H replaceable by D$_2$O).

EXAMPLE 32

3,5-Dihydroxy-α-[[[2-[4-(5-(2-oxo-tetrahydrooxazolyl)methyloxy)phenyl]-1-methylethyl]amino]methyl]benzenemethanol monohydrate.

The corresponding 3,5-dibenzyloxy compound was prepared from 4-(5-(2-oxo-tetrahydrooxazolyl)methyloxy)phenylpropan-2-one and 2-hydroxy-2-(3,5-dibenzyloxyethanamine) in an analogous manner to the compound described in Example 27. This was dissolved in ethyl acetate and hydrogenated at atmospheric pressure in the presence of 10% Palladium on carbon. The reaction mixture was filtered and evaporated to a foam which was recrystallised from ethyl acetate/methanol to give 3,5-Dihydroxy-α-[[[2-[4-(5-(2-oxo-tetrahydrooxazolyl)methyloxy)phenyl]-1-methylethyl]amino]methyl]benzenemethanol monohydrate, m.p. 88°-100° C., as a 1:1 mixture of diastereoisomers.

$^1$H NMR (DMSO-d$_6$) ppm:
0.96(d,3H); 2.60-4.10(m,9H+4H replaceable by D$_2$O); 4.23-4.70(m,1H); 4.75-5.10(m,1H); 6.00-6.30(m,3H); 6.75-7.30(q,4H); 7.55(s,1H replaceable by D$_2$O); 9.10 (broad, 2H replaceable by D$_2$O).

EXAMPLE 33

4-Amino-3,5-dichloro-α-[[[2-[4-(5-(2-oxo-tetrahydrooxazolyl)methyloxy)phenyl]-1-methylethyl]amino]methyl]benzenemethanol.

4-Amino-3,5-dichloro-α-[[[2-[4-(5-(2-oxo-tetrahydrooxazolyl)methyloxy)phenyl]-1-methylethyl]amino]methyl]benzenemethanol was prepared as a 1:1 mixture of diastereoisomers, m.p. 85°–105° C. from 4-(5-(2-oxo-tetraydrooxazolyl)methyloxy)phenylpropan-2-one and 2-hydroxy-2-(4-amino-3,5-dichlorophenyl) ethanamine in an analogous manner to the compound described in Example 27.

$^1$H NMR (CDCl$_3$) ppm:
1.00(d,3H); 2.45–3.80(m,5H+4H replaceable by D$_2$O) 4.05(d,2H); 4.32–4.70(m,3H); 4.75–5.05(m,1H); 6.70–7.20(m,6H+1H replaceable by D$_2$O).

EXAMPLE 34

3,5-Dihydroxy-α-[[[2-[4-(2-(5-oxomorpholinyl)methyloxy)phenyl]-1-methylethyl]amino]methyl]benzenemethanol, monohydrate.

The corresponding 3,5-dibenzyloxy compound was prepared from 4-(2-(5-oxomorpholinyl)methyloxy)phenylpropan-2-one and 2-hydroxy-2-(3,5-dibenzyloxyphenyl)ethanamine in an analogous manner to the compound described in Example 29. This was dissolved in ethyl acetate (80 ml) and hydrogenated at atmospheric pressure in the presence of 10% palladium on carbon. The reaction mixture was filtered and evaporated to a foam which was recrystallised from ethyl acetate-methanol to give 3,5-dihydroxy-α-[[[2-[4-(2-(5-oxomorpholinyl)methyloxy)phenyl]-1-methylethyl]amino]methyl]benzenemethanol, monohydrate m.p. 85°–106° C., as a 55:45 mixture of diastereoisomers.

$^1$H NMR (DMSO-d$_6$) ppm:
0.95(d,3H); 2.60–3.00(m,5H); 3.10–3.85(m,2H+4H replaceable by D$_2$O); 3.90–4.25(m,5H); 5.45(m,1H); 6.05–6.25(m,3H); 6.75–7.25(q,4H); 8.00(s,1H replaceable by D$_2$O); 9.10 (broad, 2H replaceable by D$_2$O).

EXAMPLE 35

4-Amino-3,5-dichloro-α-[[[2-[4-(2-(5-oxomorpholinyl)methyloxy)phenyl]-1-methylethyl]amino]methyl]benzenemethanol.

4-Amino-3,5-dichloro-α-[[[2-[4-(2-(5-oxomorpholinyl)methyloxy)phenyl]-1-methylethyl]amino]methyl]benzenemethanol was prepared from 4-(2-(5-oxomorpholinyl)methyloxy)phenylpropan-2-one and 2-(4-amino-3,5-dichlorophenyl)-2-hydroxyethananine as a 46:54 mixture of diastereoisomers m.p. 144°–160° C. in an analogous manner to the compound described in Example 29.

$^1$H NMR (DMSO-d$_6$) ppm:
1.08(d,3H); 2.1(broad,4H replaceable by D$_2$O); 2.50–2.75(m,3H); 2.78–2.98(m,2H); 3.45–3.60(m,2H); 3.95–4.17(m,3H); 4.37–4.55(m,3H); 6.28(s,1H replaceable by D$_2$O); 6.83(q,2H); 7.08(q,2H); 7.15(d,2H).

EXAMPLE 36

3,4-Dichloro-α-[[[2-[4-(5-(2-oxotetrahydrooxazolyl)methyloxy)phenyl]-1-methylethyl]amino]methyl]benzenemethanol.

3,4-Dichloro-α-[[[2-[4-(5-(2-oxotetrahydrooxazolyl)methyloxy)phenyl]-1-methylethyl]amino]methyl]benzenemethanol, m.p. 128°–136° C. (ethylacetate/ether) was prepared as a 70:30 mixture of diastereoisomers from 4-(5-(2-oxo-tetrahydrooxaolyl)methyloxy)phenylpropan-2-one (1.08 g) and 2-(3,4-dichlorophenyl)-2-hydroxyethanamine (0.89 g) in an analogous manner to the compound described in Example 27.

$^1$H NMR (CDCl$_3$+DMSO-d$_6$) ppm:
0.96(3H,d); 2.3–3.0(6H,m); 3.25–3.8(3H,m); 4.1(2H,d); 4.55(1H,t); 4.85(1H,m); 6.8(2.H,d); 6.9–7.6(6H,m).

EXAMPLE 37

(R*,R*)-(±)-3,4-Dichloro-α-[[[2-[4-(2-(4,5-dihydrothiazolyl)methyloxy)phenyl]-1-methylethyl]amino]methyl]benzenemethanol, hydrochloride, monohydrate.

(R*,R*)-(±)-3,4-Dichloro-α-[[[2-[4-(2-(4,5-dihydrothiazolyl)methyloxy)phenyl]-1-methylethyl]amino]methyl]benzenemethanol, hydrochloride, monohydrate, m.p. 108°–115° C., was prepared from (R*,R*)-(±)-methyl-4-[2-[(3,4-dichloro-β-hydroxy-phenethyl)amino]propyl]phenoxyacetate and 2-aminoethanethiol in an analogous manner to the compound described in Example 28.

$^1$H NMR (DMSO-d$_6$) ppm: 1.08(3H,d); 2.51–2.58(1H,m); 2.82(2H,t); 3.00—3.46(6H+2H replaceable by D$_2$O,m); 4.46(2H,s); 5.01–5.05(1H,m); 6.42(1H replaceable by D$_2$O,m); 6.93(2H,d); 7.16(2H,d); 7.42(1H,m); 7.68(2H,m); 8.75 (broad, 1H replaceable by D$_2$O); 9.08(broad,1H replaceable by D$_2$O).

EXAMPLE 38

6-[4-[2-[(3-Chloro-β-hydroxyphenethyl)amino]propyloxy]phenyl]-4,5-dihydro-3(2H)-pyridazinone.

A mixture of 4,5-dihydro-6-(4-acetonyloxyphenyl)3(2H)-pyridazinone (0.3 g) and 2-hydroxy-2-(3-chlorophenyl) ethanamine carbonate (0.26 g) in dry benzene (80 ml) was heated under reflux, with azeotropic removal of water, for 3 hr. The solvent was evaporated and the residue dissolved in methanol (80 ml) and treated with sodium cyanoborohydride (0.5 g). After 18 hr. the methanol was evaporated and the residue partitioned between ethylacetate and brine. The organic phase was washed with water, dried (MgSO$_4$) and evaporated to a gum which was chromatographed on silica gel. Elution with methanol-chloroform (4:96) gave 6-[4-[2-[(3-chloro-β-hydroxyphenethyl)amino]propyloxy]-phenyl]-4,5-dihydro-3(2H)-pyridazinone as a white crystalline solid, m.p.t. 140°–158° C., as a 1:1 mixture of diastereoisomers.

$^1$H NMR (CDCl$_3$) ppm:
1.20(3H,q); 2.52–2.97(7H,m,1H replaceable by D$_2$O); 3.15(1H,m); 3.99(2H,m); 4.68–5.00(1H,m plus 1H, broad, replaceable by D$_2$O); 6.90(2H,m); 7.26(3H,m); 7.41(1H,s); 7.67(2H,d); 9.82(1H,s, replaceable by D$_2$O).

EXAMPLE 39

6-[4-[2-[(4-β-Dihydroxyphenethyl)amino]propyloxy]phenyl]-4,5-dihydro-3(2H)-pyridazinone.

A suspension of 6-[4-[2-[(4-benzyloxy-β-hydroxyphenethyl)amino]propyloxy]phenyl]-4,5-dihydro-3(2H)-pyridazinone (0.35 g) in methanol (50 ml) was hydrogenated at atmospheric pressure in the presence of 10% palladium on carbon. The reaction mixture was filtered and evaporated to a white solid which was recrystallised from methanol to give 6-[(4-[2-[(4-β-dihydroxyphenethyl)amino]propyloxy]-phenyl]-4,5-dihydro-3(2H)-pyridazinone m.pt. 200°-212° C. as a 65:35 mixture of diastereoisomers.

¹H NMR (DMSO-d₆) ppm:
1.05(3H,m); 2.41(2H,t); 2.55-2.73(2H,m); 2.90(2H,t); 3.01(1H,m); 3.85(2H,m); 4.48,(1H,m); 5.03-5.09(1H,m, replaceable by D₂O); 6.68(2H,d); 6.93(2H,d); 7.13(2H,d); 7.67(2H,d); 9.18(1H,s, replaceable by D₂O); 10.77(1H,s, replaceable by D₂O).

EXAMPLE 40

5-[4-[2-[(3-Chloro-β-hydroxyphenethyl)amino]propyloxy]phenyl]-3,4-dihydro-6-methyl-2(1H)-pyridinone.

5-[4-[2-[(3-Chloro-β-hydroxyphenethyl)amino]propyloxy]phenyl]-3,4-dihydro-6-methyl-2(1H)-pyridinone was prepared as a 1:1 mixture of diastereoisomers, m.pt. 99°-104° C., from 2-hydroxy-2-(3-chlorophenyl)ethanamine carbonate (0.58 g) and 3,4-dihydro-5-(4-acetonyloxyphenyl) 6-methyl-2(1H)-pyridinone (0.75 g) in an analogous manner to the compound described in Example 38.

¹H NMR (CDCl₃ +D₂O) ppm:
1.20(3H,m); 1.84(3H,s); 2.53-2.75(5H,m); 2.95-3.18(2H,m); 3.79-3.96(2H,m); 4.66(1H,m); 6.85(2H,m); 7.10(2H,m); 7.25-7.38(4H,m).

EXAMPLE 41

6-[4-[2-[(3-Chloro-β-hydroxyphenethyl)amino]propyl]phenyl]-4,5-dihydro-3(2H)-pyridazinone, hemihydrate.

6-[4-[2-[(3-Chloro-β-hydroxyphenethyl)amino]propyl]phenyl]-4,5-dihydro-3(2H)-pyridazinone, hemihydrate was prepared as a 45:55 mixture of diastereoisomers, m.pt. 49°-50° C., from 2-hydroxy-2-(3-chlorophenyl) ethanamine carbonate (0.16 g) and 4,5-dihydro-6-[4-acetonyl)phenyl]-3(2H)-pyridazinone(0.18 g) in an analagous manner to the compound prepared in Example 38.

¹H NMR (DMSO-d₆) ppm:
0.92(3H,d); 2.40-2.95(1 OH,m, 1H replaceable by D₂O); 3.30(1H, broad, replaceable by D₂O); 4.59(1H,m); 5.36(1H, broad, replaceable by D₂O); 7.18-7.67(8H,m); 10.84(1H,s, replaceable by D₂O).

EXAMPLE 42

4-Hydroxy-α-[[[2-[4-((4,5-dihydro-1H-2-imidazolyl)methyloxy)phenoxy]-1-methylethyl]amino]methyl]benzenemethanol.

A solution of 4-benzyloxy-α-[[[2-[4-((4,5-dihydro-1H-2-imidazolyl)methyloxy)phenoxy]-1-methylethyl]amino]methyl]benzenemethanol (1.5 g) in ethylacetate (80 ml) was hydrogenated at atmospheric pressure in the presence of 10% palladium on carbon. The reaction mixture was filtered and evaporated to a foam which was purified by column chromatography on alumina. Elution with methanol-chloroform (8:92) gave 4-hydroxy-α [[[2-[4-((4,5-dihydro-1H-2-imidazolyl)-methyloxy)phenoxy]-1-methylethyl]amino]methyl]benzene-methanol m.pt. 160°-180° C. (ethyl acetate), as a 40:60 mixture of diastereoisomers.

¹H NMR (DMSO-d₆) ppm:
1 02(q,3H); 2.55-2.75(m,2H); 2.93(m,1H); 3.25-3.50(m,4H+2H replaceable by D₂O); 3.66-3.72(m,2H); 4.42-4.57 (s+m,3H); 5.15(m,1H replaceable by D₂O); 6.68(d,2H); 6.76-6.93(m,4H); 7.12(d,2H); 9.3 (broad,1H replaceable by D₂O).

EXAMPLE 43

5-[4-[2-[(3-Chloro-β-hydroxyphenethyl)amino]propyl]phenyl]-3,4-dihydro-6-methyl-2(1H)-pyridinone.

A mixture of 2-hydroxy-2-(3-chlorophenyl)ethanamine carbonate (0.34 g) and 3,4-dihydro-5-(4-acetonylphenyl)-6-methyl-2(1H)-pyridone (0.4 g) was dissolved in methanol (30 ml). Sodium cyanoborohydride (0.1 g) was added and the mixture was allowed to stand at room tempeature for 16 hr. The solvent was evaporated, the residue partitioned between ethylacetate and water, the organic layer separated, dried (MgSO₄) and evaporated to give an oil which was chromatographed on Silica. Elution with methanol-chloroform (3:97) gave 5-[4-[2-[(3-chloro-β-hydroxyphenethyl)amino]propyl]phenyl]-3,4-dihydro-6-methyl-2(1H)-pyridinone as a 1:1 mixture of diastereoismers, m.pt. 103°-106° C. (ethyl acetate ether).

¹H NMR (DMSO-d₆) ppm:
0.93(3H,d); 1.76(3H,d) 2.35-2.59(5H,m); 2.61-2.79(3H,m); 2.81-2.88(1H,m), 3.3(1H, disappears with D₂O); 4.59(1H,t); 5.35(1H, disappears with D₂O); 7.10(4H,d); 7.24-7.35(3H,M); 7.37(1H,s); 9.10(1H, disappears with D₂O).

EXAMPLE 44

2-Amino-5-[4-[2-[(3-trifluoromethyl-β-hydroxyphenethyl)amino]propyl]phenyl]-oxazol-4-one.

To a solution of methyl 4-[2-[(3-trifloromethyl-β-hydroxyphenethyl)amino]propyl]mandelate (1.5 g) and guanidine hydrochloride (0.35 g) in methanol at room temperature was added a solution of sodium (0.084 g) in methanol. The solution was heated under reflux for 2 h., cooled, filtered and the solvent removed in vacuo. The residue was partitioned between ethyl acetate, and water, the organic layer separated, dried (magnesium sulphate), and evaporated to an oil which was chromatographed on silica. Elution with chloroform:methanol (95:5) gave 2-amino 5-[4-[2[(3-trifluoromethyl-β-hydroxyphenethyl)amino]propyl]phenyl]oxazol-4-one (0.45 g) as a 40:60 mixture of diastereoisomers, m.p. 152°-164° C. (acetone).

¹H NMR (DMSO-d₆) ppm:
1.0(3H,d); 2.4-3.2(5H,m); 4.2-6.3(3H, very broad, exchanges with D₂O ); 4.8(1H,m); 5.7(1H,s); 7.3(4H,m); 7.6-7.9(4H,m ; 8.0-9.0(1H, very broad, exchanges with D₂O.

EXAMPLE 45

1-[10-[4-[2-[(3-Trifluoromethyl-β-hydroxyphenethyl)amino]propyl]phenoxy]decyl]pyrazolidin-3-one, dihydrobromide.

A solution of 1-[10-(4-acetonylphenoxy)decyl]-pyrazolidin-3-one (0.66 g and 3-trifluoromethyl-β-hydroxyphenethylamine (0.36 g) in benzene, was heated under reflux for 3 hr. using a Dean and Stark head. The reaction was cooled, the solvent removed in vacuo and the residue was dissolved in methanol, cooled to <5° C., treated with sodium borohydride (0.1 g), and stirred for 3 hr. The solvent was removed in vacuo, the residue partitioned between ethylacetate and water, the organic layer separated, dried (MgSO₄) and evaporated to an oil which was chromatographed on silica. Elution with chloroform: methanol (97:3) gave an oil which was dissolved in ether and treated with hydrogen bromide to give 1-[10[4-[2-[(3-trifluoromethyl-β-hydroxyphenethyl)-amino]propyl-phenoxy]-decyl]pyrazolidin-3-one, dihydrobromide (0.65 g) as a (45:55) mixture of diastereoisomers, m.p. 141°-150° C.(ethanol-ether).

$^1$H NMR (DMSO-d$_6$+D$_2$O) ppm:
1.1(3H,d); 1.2–1.5(12H,m); 1.5–1.8(4H,m); 2.5–3.0(3H,m); 3.0–3.6(6H,m); 3.6–4.5(2H, broad); 3.9(2H,t); 5.2(1H,m); 6.8(2H,d); 7.2(2H,d); 7.6–7.8(4H,m).

EXAMPLE 46

3-Trifluoromethyl-α-[[[2-[4-(1-benzyl-1,2,3,6-tetrahydropyridyl)phenyl]-1-methylethyl]amino]methyl] benzenemethanol, dihydrochloride.

A solution of 4-(1-benzyl-1,2,3,6-tetrahydropyridyl) phenyl propan-2-one (1.5 g and 3-trifluoromethyl-β-hydroxyphenethylamine 1.03 g) in benzene (100 ml) was heated under reflux for 5 hr. using a Dean and Stark head. The cooled solution was evaporated in vacuo, the residue dissolved in methanol, cooled to <5° C. and treated with sodium borohydride (0.2 g). The reaction mixture was stirred for 1.5 hr. and the solvent removed in vacuo. The residue was partitioned in beteen ethyl acetate and water, the organic layer separated, dried (magnesium sulphate), and the solvent evaporated to an oil which was chromatographed on silica. Elution with chloroform:methanol (98.2) gave an oil which was dissolved in ethanol and treated with ethereal hydrogen chloride to give 3-trifluoromethyl-α-[[[2-[4-(1-benzyl-1,2,3,6-tetrahydropyridyl)phenyl]-1-methylethyl]amino]methyl] benzenemethanol, dihydrochloride a 42:58 mixture of diastereoisomers, m.p. 215°-237° C.

$^1$H NMR (DMSO-d$_6$) ppm:
1.2(3H,d); 2.6–4.0(11H,m); 4.4(2H,s); 5.2(1H,m); 6.2(1H,s); 6.5(1H, broad, exchanges with D$_2$O); 7.1–8.0(13H,m); 9.1 (1H, broad, exchanges with D$_2$O); 9.9 (1H, broad, exchanges with D$_2$O); 11.7 (1H, broad exchanges with D$_2$O).

EXAMPLE 47

3-Trifluoromethyl-α-[[[2-[4-(1,2,3,6-tetrahydropyridyl)-phenyl]-1-methylethyl]amino]methyl]benezenemethanol, dihydrochloride.

This compound was prepared from 4-(1,2,3,6-tetrahydropyridyl)phenylpropan-2-one and 3-trifluoromethyl-β-hydroxyphenethylamine in an analogous manner to the compound described in Example 46.

$^1$H NMR (DMSO-d$_6$) ppm:
1 2(3H,d); 2.6–2.9(2H,m) 2.9–4.0(9H,m) 5.1–5.3(1H,m); 6.2(1H,s); 6.2–6.8(1H, broad, exchanges with D$_2$O); 7.1–7.6 (4H,dd); 7.6–8.0 (4H,m); 8.8–9.5 (1H, broad, exchanges with D$_2$O); 9.5–10.4 (3H, broad, exchanges with D$_2$O).

EXAMPLE 48

2-Amino-5-[4-[2-[(β-4-dihydroxyphenethyl)amino]-propoxy]phenyl]oxazol-4-one

2-Amino-5-[4-[2-[(4-benzyloxy-β-hydroxyphenethyl)amino]propoxy]phenyl]oxazol-4-one was prepared from methyl 4-[2-[(4-benzyloxy-β-hydroxyphenethyl)amino]propyl]mandelate and guanidine hydrochloride by the procedure described in example 44. Debenzylation was carried out using glacial acetic acid as solvent by the procedure described in Example 42 and the residual oil was chromatographed on silica. Elution with chloroform:methanol:ammonia (91:8:1) gave 2-amino-5-[4-[2-[(β-4-dihydroxyphenylethyl)amino]propoxy]-phenyl]oxazol-4-one as a 48:52 mixture of diastereoisomers, m.p. 96°–107° C.

$^1$H NMR (DMSO-d$_6$) ppm:
1.05 (3H,m); 3.1–3.4(4H,m); 3.8(2H,m); 4.45(1H,m); 5.05(1H,m, exchanges with D$_2$O; 5.6(1H,m); 6.7(2H,d); 6.9(2H,m); 7.1–7.3(4H,m) 7.7–8.8(2H,broad, exchanges with D$_2$O); 9.2(1H,s, exchanges with D$_2$O).

EXAMPLE 49

Methyl 5-[4-[2-[(3-chloro-β-hydroxyphenethyl)amino]propyl]-phenoxy]furan-2-carboxylate, hydrochloride.

A mixture of methyl 5-[4-acetonylphenoxy]furan-2-carboxylate (1.04 g) and 2-hydroxy-2-(3-chlorophenyl)ethanamine (0.65 ) in dry benzene (100 ml) was heated under reflux, with azeotropic removal of water, for 1 hr. the solvent was evaporated and the residue dissolved in methanol (100 ml), cooled, and treated with sodium borohydride (0.4 g), in portions. The reaction mixture was stirred at ambient temperature for 2 hr. The solvent was evaporated and the residue partitioned between water and chloroform. The organic layer was dried (MgSO$_4$) and evaporated to an oil which was purified by column chromatography on silica gel. Elution with 4% methanol:chloroform gave a colourless oil. An ethereal solution of the free base was treated with hydrogen chloride gas to give methyl 5-[4-[2-[(3-chloro-β-hydroxyphenethyl)amino]propyl]phenoxy]furan-2-carboxylate, hydrochloride as a 65:35 mixture of diastereoisomers, m.p. 148°–150° C. (ethylacetate-ether).

$^1$H NMR (DMSO-d$_6$) ppm:
1.15(3H,d); 2.63–3.60(6H,m,1H replaceable by D$_2$O); 3.78(3H,s); 5.10 (1H,m); 5.88(1H,d); 6.34(1H,m, replaceable by D$_2$O); 7.10–7.50(9H,m); 9.16(1H, broad, replaceable by D$_2$O).

EXAMPLE 50

Methyl 5-[4-[2-[(3-chloro-β-hydroxyphenethyl)amino]propyl]-phenoxymethyl]furan-2-carboxylate A mixture of methyl 5-[4-acetonylphenoxymethyl]furan-2-carboxylate (1.76 g) and 2-hydroxy-2-(3-chlorophenyl) ethanamine (1.05 g) in dry benzene (100 ml) was heated under reflux with azeotropic removal of water, for 2 hr. The solvent was evaporated and sodium borohydride (2 g) added, in portions, to a stirred solution of the residual oil in methanol (80 ml) with cooling in ice. The mixture was stirred at ambient temperature for 3 hr. the solvent was evaporated and the residue was partitioned between water and dichloromethane. The organic layer was dried (MgSO$_4$) and evaporated to an oil which was purified by column chromatography on silica gel. Elution with methanol:chloroform (4:96) gave an oil which was crystallised from n-hexane to give methyl 5-[4-[2-[(3-chloro-β-hydroxyphenethyl)amino]propyl]phenoxymethyl]furan-2-carboxylate, m.pt 75°–86° C., as a 19:81 mixture of diastereoisomers. The mother liquor was evaporated; crystallisation from Petroleum ether (60:80)—ether gave a second crop, m.pt. 75°–83° C., as a 55:45 mixture of diastereoisomers.

$^1$H NMR (CDCl$_3$) ppm:
1 07(3H,d); 2.08(2H broad, replaceable by D$_2$O); 2.55–3.10(5H,m); 3.90(3H,s); 4.60(1H,m); 5.02(2H,s); 6.53(1H,d); 6.81–7.40(9H,m).

EXAMPLE 51

3-Chloro-α-[[[2-[4-(5-(2-methylaminomethyl)furylmethyloxy)phenyl]-1-methylethyl]amino]methyl]benzenemethanol, dihydrochloride.

Methyl 5-[4-[2-[(3-chloro-β-hydroxyphenethyl)amino]propyl]phenoxymethyl]furan-2-carboxamide (1.14 g) in dry tetrahydrofuran (20 ml was added, dropwise, under a nitrogen atmosphere, to a stirred slurry of lithium aluminium hydride (0.7 g) in dry tetrahydrofuran (30 ml). The resulting mixture was stirred and heated under reflux for 2 h, cooled in ice and treated with water (0.7 g), 2N sodium hydroxide solution (0.7 g), water (2.1 g) and chloroform (50 ml). The mixture was filtered and the filtrate evaporated to an oil which was purified by column chromatography on silica gel. Elution with methanol:chloroform (5:95) gave a colourless oil which was treated with ethereal hydrogen chloride to give 3-chloro-α-[[[2-[4-(5-(2-methylaminomethyl)furylmethyloxy)phenyl]-1-methylethyl]amino]methyl]benzenemethanol, dihydrochloride as a 52:48 mixture of diastereoisomers, m.p. 190°–195° C. (ethylacetate-methanol).

$^1$H NMR (DMSO-$d_6$) ppm:
1.12(3H,d); 2.51(3H,s); 3.07–3.50(7H,m,2H replaceable by $D_2O$); 4.18(2H,s); 5.10(2H,s plus 1H,m); 6.63(2H,s); 7.08(4H,q); 7.46(4H,m); 9.32(3H, broad, replaceable by $D_2O$).

EXAMPLE 52

2-Amino-5-[4-[2-[(3-trifluoromethyl-β-hydroxyphenethyl]amino]propyl]phenoxymethyl]-4,5-dihydrooxazole, fumarate, hemihydrate.

2-Amino-5-[4-[2-[(3-trifluoromethyl-β-hydroxyphenethyl)amino]propyl]phenoxymethyl]-4,5-dihydrooxazole, fumarate, hemihydrate was prepared as a 1:1 mixture of diastereoisomers, m.p. 140°–149° C. (ethylacetatemethanol) from 2-amino-5-(4-acetonylphenoxymethyl]4,5-dihydrooxazole and 2-hydroxy-2-(3-trifluoromethylphenyl)ethanamine in an analogous manner to the compound prepared in Example 49.

$^1$H NMR (Free-Base, $CDCl_3$) ppm:
1.02(3H,d); 2.33–3.00(5H,m); 3.40–4.95(1 OH,m, 4H replaceable by $D_2O$); 6.68–7.10 (4H,q); 4.43–7.60(4H,m).

EXAMPLE 53

3-Chloro-α-[[[2-[4-(5-(2-methylaminomethyl)tetrahydrofurylmethyloxy)phenyl]-1-methylethyl]amino]methyl]benzenemethanol, dihydrochloride, hemihydrate.

3-Chloro-α-[[[2-[4-(5-(2-methylaminomethyl)tetrahydrofurylmethyloxy)phenyl]-1-methylethyl]amino]methyl]benzenemethanol, dihydrochloride, hemihydrate was prepared as a 48:52 mixture of diastereoisomers, m.p. 60°–80° C. from methyl 5-[4-[2-[(3-chloro-β-hydroxyphenethyl)amino]propyl]phenoxymethyl]tetrahydrofuran-2-carboxamide, in an analogous manner to the compound described in Example 51.

$^1$H NMR (DMSO-$d_6$) ppm: 1.12
(3H,m); 1.58–2.20(4H,m); 2.54(3H,s); 2.73–3.44(7H,m,2H replaceable by $D_2O$); 3.90–4.28 (4H,m); 5.16(1H,m); 6.36(1H,m, replaceable by $D_2O$); 6.90–7.24(4H,q); 7.42–7.52(4H,m); 9.20(3H,m, replaceable by $D_2O$).

EXAMPLE X1

4-[4-Acetonylphenoxy]-3-hydroxy-1H-pyrrole-2,5-dione.

A solution of 4-acetonylphenoxyacetamide, ethylene ketal (3.2 g) and diethyl oxalate (2.0 g) in dry dimethylformamide at 0° C. was treated with potassium tert-butoxide (3.24 g) in two portions at 15 min. intervals. The solution was then stirred 16 h at ambient temperature, poured into water, and acidified with 6N hydrochloric acid. The aqueous solution was extracted with ethyl acetate, the combined organic extracts dried (magnesium sulphate), filtered and evaporated and the residue crystallised from acetone/ether to give 4-[4-acetonylphenoxy]-3-hydroxy-1H-pyrrole-2,5-dione, (1.5 g).

$^1$H NMR ($CDCl_3$ and DMSO-$d_6$):
2.2(3H,S); 3.6(2H,s); 7.0(4H,m);9.8(1H,s+1H very broad).

This material was converted to the sodium salt by treatment with an equivalent of sodium hydroxide in aqueous solution, evaporating to dryness and azeotroping residual water with benzene. The sodium salt was used without further purification.

EXAMPLE X2

2-(4-Acetonylphenoxymethyl)-5-benzyloxy-4H-pyran-4-one, ethylene ketal

A mixture of 4-hydroxyphenylpropan-2-one, ethylene ketal (3.88 g), 5-benzyloxy-2-chloromethyl-4H-pyran-4-one (5.0 g) and potassium carbonate 3.5 g) in acetone, was heated under reflux for 18 h. The reaction mixture was cooled, filtered and the solvent removed in vacuo. The residue was dissolved in ethyl acetate, washed with 2N-sodium hydroxide solution (1×50 ml), water (2×50 ml), dried (magnesium sulphate), filtered and evaporated to dryness in vacuo. The residue was purified by column chromatography on silica using chloroform as eluent, followed by crystallisation from acetone to give 2-(4-acetonylphenoxymethyl)-5-benzyloxy-4H-pyran-4-one ethylene ketal, (5.3 g).

$^1$H NMR ($CDCl_3$) ppm:
1.3(3H,s);2.8(2H,s);3.8(4H,m);4.8 (2H,s);5.1(2H,s); 6.55(1H,s);6.8(2H,d);7.2(2H,d);7.35(5H,s);7.6(1H,s).

EXAMPLE X3

2-(4-Acetonylphenoxymethyl)-5-hydroxy-4$\underline{\text{H}}$-pyran-4-one

A solution of 2-(4-acetonylphenoxymethyl)-5-benzyloxy-4H-pyran-4-one, ethylene ketal (2.0 g) in methanol was hydrogenated at ambient temperature and pressure over 10% palladium on carbon until absorption of hydrogen was complete. The catalyst was filtered off and the solvent removed in vacuo. The residue was dissolved in acetone (75 ml) and treated with 2N-hydrochloric acid solution (2 ml) and allowed to stand at room temperature for 2 h. The solvent was then removed in vacuo, the residue dissolved in ethyl acetate, washed with water (2×50 ml), brine (1×50 ml) and dried (magnesium sulphate). After filtration and evaporation of the solvent, the residue was purified by column chromatography on silica using methanol-chloroform (2:98) as eluent to give 2-(4-acetonylphenoxymethyl) -5-hydroxy-4H-pyran-4-one, (1.2 g).

$^1$H NMR ($CDCl_3$) ppm:

2.15(3H,s);3.65(2H,s);4.8(2H,s);6.65(1H,s);7.0(4H,dd); 7.9(1H,s).

EXAMPLE X4

Ethyl 3-(4-acetonylphenyl)-2-chloropropionate, ethylene ketal

A solution of ethyl 2-chloroacetoacetate (8.25 g) in dry dimethylformamide was treated with sodium hydride (1.3 g and stirred at ambient temperature for 0.5 h. A solution of 4-(bromomethyl)phenylpropan-2-one, ethylene ketal (12.0 g) in dry dimethylformamide (20 ml) was then added and the mixture was heated at 70° C. for 4 h. The reaction mixture was cooled, poured into ice/water, acidified with 2N-hydrochloric acid, extracted with ethyl acetate (4×50 ml) and the combined organic extracts dried (magnesium sulphate), filtered and evaporated in vacuo. The residue was dissolved in ethanol and treated at 0°-5° C. with barium hydroxide hydrate (7.7 g). The mixture was stirred for 0.5 h, poured into ice/water, extracted with ethyl acetate (3×50 ml) and the combined organic extracts dried (magnesium sulphate), filtered and evaporated in vacuo to leave a red oil, which was purified by column chromatography on silica using diethyl ether: petroleum ether (60°-80°) (30:70) as eluent to give ethyl 3-(4-acetonylphenyl)-2-chloropropionate, ethylene ketal, (6.0 g).

'H NMR (CDCl$_3$)ppm:
1.2(3H,t);1.25(3H,s);2.8(2H,s)3.2(2H,dd);3.8(4H,m); 4.2(2H,q);4.3(1H,m);7.2(4H,s).

EXAMPLE X5

5-(4-Acetonylbenzyl)-2-iminothiazolidine-4-one

A mixture of ethyl 3-(4-acetonylphenyl)-2-chloropropionate, ethylene ketal (4.86 g), thiourea (1.19 g) and sodium acetate (1.29 g) in 2-methoxyethanol (25 ml) was stirred and heated at 100 ° C. for 16 h. The solvent was evaporated and the residue was diluted with 50:50 water/hexane (50 ml). The resulting solid was filtered, dried and purified by chromatography on silica gel. Elution with methanol:chloroform (4:96) gave 5-(4-acetonylbenzyl)-2-iminothiazolidine-4-one as a white solid, mp 196°-198° C.

'H NMR (CDCl$_3$)ppm:
2.20(3H,s);2.95-3.50(2H,m);3.70-4.04(2H,s+2H, broad, exch.D$_2$O);4.55 (1H,m);7.20(4H,s).

EXAMPLE X6

5-(4-Acetonylbenzyl)thiazolidine-2,4-dione 5-(4-Acetonylbenzyl)-2-iminothiazolidine-4-one (1g) was heated under reflux in a mixture of 2-methoxyethanol 20 ml and 2N HCl (5 ml) for 8 h. The cooled mixture was diluted with water and the resulting precipitate filtered and dried under vacuum to give 5-(4-acetonylbenzyl)thiazolidine-2,4-dione as a white solid, mp 133°-135° C.

'H NMR (CDCl$_3$)ppm:
2.20(3H,s);3.08-3.55(2H,m);3.72(2H,s);4.55(1H,m); 7.27(4H,s);9.15(1H,broad, exch.D$_2$O).

EXAMPLE X7

4-Acetonylphenoxyacetonitrile

A mixture of 4-hydroxyphenylpropan-2-one, ethylene ketal (4.7 g), potassium carbonate (3.5 g) and chloroacetonitrile (1.83 g) in acetone, was heated under reflux for 5 h, cooled, filtered, and treated with 2N hydrochloric acid (1 ml). The solution was allowed to stand at room temperature for 4 h, the solvent was evaporated in vacuo and the residue partitioned between ethylacetate and water. The organic layer was dried, (magnesium sulphate), filtered and evaporated. The residue was purified by column chromatography on silica using chloroform as eluent to give 4-acetonylphenoxyacetonitrile, (3.0 g)

'H NMR (CDCl$_3$)ppm:
2.2(3H,s);3.7(2H,s);4.75(2H,s);7.1(4H,dd).

EXAMPLE X8

4-[2-[(3-Chloro-β-hydroxyphenethyl)amino]propyl]-phenoxyacetonitrile

A mixture of 2-(3-chlorophenyl)-2-hydroxyethylamine carbonate (3.35 g) and 4-acetonylphenoxyacetonitrile in benzene was heated under reflux for 1 h with azeotropic removal of water using a Dean and Stark head. The solution was cooled, and the solvent removed in vacuo. The residue was dissolved in methanol and treated with sodium cyanoborohydride (1.25 g) and stirred for 5 h at ambient temperature. The solvent was then evaporated under reduced pressure, the residue dissolved in ethyl acetate, washed with water (2×50 ml), brine (1×50 ml), dried (magnesium sulphate), filtered and evaporated. The residue was purified by column chromatography on silica using methanol:chloroform 2:98 as eluent to give 4-[2-[(3-chloro-β-hydroxyphenethyl)amino]propyl] phenoxyacetonitrile, (4.0 g).

'H NMR (CDCl$_3$)ppm:
0.9(3H,d);2.3-3.0(5H,m);3.0-3.7(2H,m);4-.4-4.7(1H,m); 4.6(2H,s);6.7-7.4(8H,m).

EXAMPLE X9

5-(4-Acetonylphenyl)tetrazole

A mixture of 4-cyanophenylacetone (17.0 g), ethanediol (6.6 g) and 4-toluenesulphonic acid (0.5 g) in benzene was heated under reflux with azeotropic removal of water, using a Dean and Stark head, for 18 h. The reaction mixture was cooled and the solvent removed in vacuo. The residue was partitioned between ethylacetate and water, the organic layer dried, (magnesium sulphate), filtered and evaporated. The residue was purified by column chromatography on silica using ether: petrol (50:50) as eluent to give 4-cyanophenylacetone, ethylene ketal (11.5 g). This material (5 g) was dissolved in dry dimethylformamide (50 ml) and treated with sodium azide (1.6 g), ammonium chloride (1.34 g) and heated at 100° C. for 18 h. The solvent was removed in vacuo, the residue dissolved in water, acidified to pH2(HCl) and filtered. The solid material was dissolved in ethyl acetate, dried, (magnesium sulphate), filtered and evaporated. The residue was crystallised from ethanol to give 5-(4-acetonylphenyl)tetrazole, 3.6 g.

'H NMR (DMSO-d$_6$)ppm:
2.2(3H,s);3.85(2H,s);7.35(2H,d);7.95(2H,d);14.8-16.3 (1H, very broad).

EXAMPLE X10

Methyl 3-(4-acetonylphenyl)-2,3-dibromopropionate, ethylene ketal.

A stirred solution of methyl 4-acetonyl cinnamate, ethylene ketal (5.24 g) in dry carbon tetrachloride (150 ml) at 5° C., was treated dropwise with a solution of bromine (3.2 g) in dry carbon tetrachloride (70 ml) over 0.5 h. The solution was then washed with 10% sodium hydrogen carbonate solution, dried (magnesium sulphate), filtered and evaporated to dryness to give methyl 3-(4-acetonylphenyl)-2,3-dibromopropionate, ethylene ketal, (6.4 g).

$^1$H NMR (CDCl$_3$) ppm:
1.3(3H,s);2.9(2H,s);3.8(4H,m);3.9(3H,s);4.8(1H,d); 5.4(1H,d);7.3(4H,s).

EXAMPLE X11

5-(4-Acetonylphenyl)-3-hydroxyisoxazole

A solution of methyl 3-(4-acetonylphenyl)-2,3-dibromopropionate, ethylene ketal (4.2 g) in methanol (25 ml) was added dropwise to a stirred mixture of hydroxylamine hydrochloride (0.86 g) and potassium hydroxide (3.9 g) in methanol: water (150 ml) at ambient temperature and stirred for 1 h. The reaction mixture was then heated under reflux for 7 h, cooled, acidified with sulphuric acid (50%), filtered, and the solvent removed under reduced pressure. The residue was partitioned between ethylacetate and water, dried (magnesium sulphate), filtered and evaporated to dryness in vacuo. The residue was purified by column chromatography on silica using chloroform as eluent, and crystallised from diethylether-(60°-80°)petroleum ether to give 5-(4-acetonylphenyl)-3-hydroxyisoxazole (0.5 g).

$^1$H NMR (CDCl$_3$ + CD$_3$OD)ppm:
2.25(3H,s);3.8(2H,s);4.6(1H,s);6.2(1H,s);7.3(2H,d); 7.8(2H,d).

EXAMPLE X12

[4-(3-Pyridylmethyloxy)phenyl]propan-2-one

A solution of (4-hydroxyphenyl)propan-2-one ethylene ketal (5 g) in ethanol (20 ml) was added to a stirred solution of sodium ethoxide in ethanol (1.26 g sodium in 50 ml). A suspension of 3-picolyl chloride hydrochloride (4.5 g) in ethanol (40 ml) was added, the mixture boiled for 4½ hr, cooled and filtered. After evaporation of the solvent the residue was chromatographed on alumina. Elution with 10% methanol in dichloromethane gave a dark oil which was dissolved in methanol (50 ml) and boiled with 2M hydrochloric acid (40 ml) for 3 hours. Neutralisation with 2M sodium hydroxide solution followed by extraction into dichloromethane yielded an oil which was purified by bulb to bulb distillation at 70° C./0.4 mm to give [4-(3-pyridylmethyloxy)phenyl]propan-2-one.

$^1$H NMR (CDCl$_3$) ppm:
2.17(s,3H), 3.66(s,2H), 5.08 (s,2H), 6.81–7.95 (m,6H); 8.53–8.81 (m,2H).

EXAMPLE X13

[4-(2-Pyridylmethyloxy)phenyl]propan-2-one

A solution of (4-hydroxyphenyl)propan-2-one ethylene ketal (28 g) in ethanol (40 ml) was added to a stirred solution of sodium ethoxide in ethanol (7.1 g of sodium in 100 ml) and the resulting solution stirred at room temperature for 20 minutes. A suspension of 2-picolyl chloride hydrochloride (25 g) in ethanol (60 ml) was added and the resulting mixture was boiled under reflux for 5 hours, cooled and filtered. 2M Hydrochloric acid (100 ml) was added, the solution boiled for 5 h, cooled and neutralised with 2M sodium hydroxide solution. After dilution with water the solution was extracted with dichloromethane and the washed organic phase dried and evaporated to give a dark oil. Bulb to bulb distillation gave [4-(2-pyridylmethyloxy)phenyl]propan-2-one, b.pt. 96°–100° C./0.2 mm, which was used without further purification.

$^1$H NMR (CDCl$_3$) ppm:
2.1 (s), 3.6 (s), 5.18 (s), 6.8–8.28 (m); 8.6 (d).

EXAMPLE X14

[4-(4-Pyridylmethyloxy)phenyl]propan-2-one

[4-(4-Pyridylmethyloxy)phenyl]propan-2-one was prepared in an analogous manner to the compound described in Example X13 from 4-picolylchloride hydrochloride.

EXAMPLE X15

4-(5-(2-Oxo-tetrahydrooxazolyl)methyloxy)phenylpropan-2-one

A solution of (4-hydroxyphenyl)propan-2-one ethylene ketal (4.77 g) in ethanol (30 ml) was added to a stirred solution of sodium ethoxide in ethanol (0.57 g sodium in 30 ml ethanol). The resulting solution was heated to reflux temperature and a suspension of 5-chloromethyl-2-oxazolidinone (3.33 g) in ethanol (30 ml) was added over 30 minutes. The resulting mixture was heated under reflux for 5 hours, cooled and filtered. The solvent was evaporated and the residue partitioned between ethyl acetate and 2N sodium hydroxide solution. The organic phase yielded an oil which was purified by column chromatography on Kieselgel 60. Elution with 2% methanol in chloroform gave a white solid which was allowed to stand in 1:1 methanol/2N hydrochloric acid (100 ml) for 8 hours. The solvent was evaporated, the residue dissolved in dichloromethane, washed with 2N sodium hydroxide solution, water, dried (MgSO$_4$) and evaporated to give 4-(5-(2-oxo-tetrahydrooxazolyl)methyloxy)phenylpropan-2-one as a white solid, m.pt 126°–130° C.

This compound has also been prepared as follows:
(4-acetonylphenoxy)-3-aminopropan-2-ol, ethylene ketal (2 g) in a solution of phosgene in toluene (40 ml of 12.5% solution) was heated to reflux temperature. Gas evolution ceased after 15 minutes; the reaction mixture was cooled and the toluene solution was decanted from a brown gum. Evaporation of the solvent gave an oil which was chromatographed on Kieselgel 60. Elution with 2% MeOH in CHCl$_3$ gave a material which was identical to that described above.

$^1$H NMR (CDCl$_3$) ppm:
2.20(s,3H); 3.50–4.25(m,6H+1H replaceable by D$_2$O); 4.85–5.20 (m,1H); 6.80–7.30 (q, 4H).

EXAMPLE X16

4-(2-(5-Oxomorpholinyl)methyloxy)phenylpropan-2-one.

A solution of (4-acetonylphenoxy)-3-aminopropan-2-ol, ethylene ketal (20.3 g) in 1,2-dichloroethane (380 ml) was added to a stirred solution of sodium hydroxide (31.46 g) in water (150 ml). The resulting mixture was cooled in ice, stirred vigorously, and treated with chloroacetylchloride (7.1 ml). The mixture was stirred at ambient temperature for 3 hrs., the organic solvent was evaporated and the aqueous residue was extracted into ethyl acetate. The organic phase was washed with water, dried (MgSO$_4$) and evaporated to an orange oil which was purified by column chromatography on Kieselgel 60 using 4% methanol in chloroform as eluent. A solution of the oil (6.88 g) in ethanol (100 ml) was treated with a solution of potassium hydroxide (2.2 g) in ethanol (30 ml) over 30 minutes. The resulting solution was stirred at ambient temperature for 24 hrs., evaporated and the residue partitioned between water and ethylacetate. The organic layer was washed with water, dried (MgSO$_4$) and evaporated to an oil which was purified by column chromatography on Kieselgel 60. Elution with 4% methanol in chloroform gave 4-(2-(5-oxomorpholinyl)-methyloxy)phenylpropan-2-one, ethylene ketal as a white solid. The solid was stirred in a methanol (50 ml) 2N hydrochloric acid (20 ml) mixture for 6 hrs. The solvent was evaporated, the residue dissolved in ethylacetate, washed with 2N sodium hydroxide solution, water, dried (MgSO$_4$) and evaporated to give 4-(2-(5-oxomorpholinyl)methyloxy)phenylpropan-2-one as a white solid, m.pt. 85°–89° C.

$^1$H NMR (CDCl$_3$) ppm:
2.15 (s,3H); 3.30–3.80(m,4H); 3.80–4.40(m,5H); 6.80–7.30(q,4H); 8.85(s,1H replaceable by D$_2$O).

EXAMPLE X17

(4-Acetonylphenoxy)-3-aminopropan-2-ol, ethylene ketal.

A solution of (4-hydroxyphenyl)propan-2-one, ethylene ketal (30 g) in ethanol (50 ml) was added to a solution of sodium hydroxide (6.18 g) in ethanol (100 ml). The resulting solution was added, over 30 minutes, to a stirred solution of epichlorohydrin (39.66 g) in dioxan (180 ml) and water (45 ml) maintained at 75°–80° C. The mixture was stirred at 75°–80° C. for a further hour after the addition was complete, cooled and filtered. The filtrate was evaporated to an oil which was partitioned between dichloromethane and water. The organic phase was dried and evaporated to an oil which was dissolved in ethanol (600 ml) containing six pellets of sodium hydroxide and treated with 0.88 ammonia solution (600 ml) enriched with ammonia gas. The resulting solution was shaken at ambient temperature in a sealed flask for 20 hrs. The solvent was evaporated to give a waxy solid. Recrystallisation from isopropanol/ether gave (4-acetonylphenoxy)-3-aminopropan-2-ol, ethylene ketal as pale yellow solid.

$^1$H NMR (CDCl$_3$) ppm:
1.30(s,3H); 2.45(s,3H replaceable by D$_2$O); 2.80–3.05(m,4H); 3.75–4.05(m,7H); 6.75–7.30(q,4H).

EXAMPLE X18

Ethyl[N-[4-[2-[(3-chloro-β-hydroxyphenyl)amino]propyl]phenyl]-N-carbomethoxymethyl]malonamide.

A mixture of 2-(3-chlorophenyl)-2-hydroxyethanamine carbonate (0.135 g, 0.33 mmol) and ethyl[N-(4-acetonylphenyl)-N-carbomethoxymethyl]malonamide (0.230 g, 0.69 mmol) in benzene (15 ml) was heated in a Dean and Stark apparatus for 2 hr. The resulting solution was cooled, concentrated in vacuo and the residue dissolved in ethanol (10 ml). Sodium cyanoborohydride (0.052 g, 0.86 mmol) was added and the solution stirred for 16 hr. The solvent was evaporated and the resulting oil was partitioned between ethylacetate and water. The organic fraction was separated, dried (magnesium sulphate) and the solvent evaporated to give an oil which was chromatographed on Silica. Elution with 95:5 chloroform/ethanol gave ethyl-[N-14-[2-[(3-chloro-β-hydroxyphenyl)amino]propyl]phenyl]-N-carbomethoxymethyl]malonamide as a colourless oil (0.29 g; 88%).

$^1$H NMR (CDCl$_3$) ppm:

1.0–1.3(6H,m); 2.45–3.0(6H,m); 3.1(2H,s); 3.65(3H,s); 4.0(2H,q); 4.25(2H,s); 4.4(2H,br hump); 7.2(8H,m).

EXAMPLE X19

Ethyl[N-(4-acetonylphenyl)-N-carbomethoxymethyl]-malonamide.

A solution of methyl N-(4-acetonylphenyl) glycinate, ethylene ketal (1.51 g, 6 mmol) in methylene chloride (30 ml) was cooled to 0° C. under an atmosphere of nitrogen. Triethylamine (1 ml, 7.5 mmol) was added to the solution followed by the dropwise addition of ethyl malonyl chloride (0.77 ml, 6 mmol) over 15 minutes. The mixture was stirred for 1 hr., poured into 2N HCl (50 ml) and the mixture stirred vigorously for 3 hr. The organic fraction was separated, washed with saturated sodium bicarbonate solution, dried (magnesium sulphate), concentrated in vacuo and the residue chromatographed on Silica. Elution with petroleum ether/ether (1:2) gave ethyl[N-(4-acetonyl-phenyl)-N-carbomethoxymethyl]malonamide (0.77 g, 41%) as a colourless oil.

$^1$H NMR (CDCl$_3$) ppm:
1.2(3H,t); 2.2(3H,s); 3.25(2H,s); 3.75(3H,s); 4.05(2H,q); 4.4(2H,s); 7.35(5H, br.s).

EXAMPLE X20

Methyl N-[4-acetonylphenyl]glycinate, ethylene ketal.

4-Aminophenylpropan-2-one, ethylene ketal (10.90 g, 0.0 1Ö?) in benzene (150 ml) was heated with methyl glyoxalate (6.14 g, 0.07 mol) in a Dean and Stark apparatus for 1 hr. The solution was allowed to cool, concentrated in vacuo and the residue dissolved in methanol (150 ml). Sodium cyanoborohydride (4.06 g 0.068 mol) was added portionwise over 0.5 hr. and the resulting mixture stirred for 16 hr. Evaporation of the solvent gave an oil which was partitioned between ethyl acetate and water. The organic layer was separated, dried (MgSO$_4$) and evaporated to give an oil which was chromatographed on Silica. Elution with an ethyl acetate/petroleum ether mixture (1:1) provided methyl N-[4-acetonylphenyl]glycinate, ethylene ketal (10.37 g, 68%) as an oil.

$^1$H NMR (CDCl$_3$) ppm: 1.3(3H,s); 2.8(2H,s); 3.7–4.3(8H,m); 6.55(2H,d); 7.15(2H,d).

EXAMPLE X21

4,5-Dihydro-6-(4-acetonyloxyphenyl)-3(2H)pyridazinone.

A mixture of 4,5-dihydro-6-(p-hydroxyphenyl)-3(2H)pyridazinone (0.55 g), chloroacetone (0.32 g) and potassium carbonate (0.4 g), with a catalytic amount of potassium iodide, was stirred and heated under reflux in acetone (60 ml) for 16 hr. The solvent was evaporated and the residue partitioned between water and ethyl acetate. The organic layer was dried (MgSO$_4$) and evaporated to a gum which was purified by chromatography on Silica gel. Elution with methanol-chloroform (4:96) gave 4,5-dihydro-6-(4-acetonyloxyphenyl)-3(2H)-pyridazinone as a pale yellow solid.

$^1$H NMR (CDCl$_3$+CD$_3$OD) ppm:
2.30(3H,s); 2.40–3.20(4H,m); 4.70(2H,s); 7.00(2H,d); 7.80(2H,d).

EXAMPLE X22

6-[4-[2-[(4-Benzyloxy-β-hydroxyphenethyl)amino]-propyloxy]phenyl]-4,5-dihydro-3(2H)-pyridazinone 6-[4-[2-[(4-Benzyloxy-β-hydroxyphenethyl)amino]-propyloxy]phenyl]-4,5-dihydro-3(2H)pyridazinone was prepared from 4,5-dihydro-6-(4-acetonyloxyphenyl)-3(2H)-pyridazinone and 2-hydroxy-2-(4-benzyloxyphenyl)ethanamine in an analogous manner to the compound described in Example 38. $^1$H NMR (DMSO-d$_6$) ppm:

1.03(3H,m); 2.28–3.20(8H,m,1H replaceable by D$_2$O); 3.82(2H,m); 4.50(1H,m); 5.00–5.22(2H,s plus 1H,m, replaceable by D$_2$O); 6.85–7.80 (13H,m); 10.81(1H,s, replaceable by D$_2$O)).

EXAMPLE X23

3,4-Dihydro-5-(4-acetonyloxyphenyl)-6-methyl-2(1H)pyridinone.

A mixture of 3,4-dihydro-5-(4-hydroxyphenyl)-6-methyl-2(1H)-pyridinone (0.94 g), chloroacetone (0.43 g) and potassium carbonate (0.64 g), with a catalytic amount of potassium iodide, was stirred and heated under reflux in acetone (80 ml) for 16 hr. The solvent was evaporated and the residue partitioned between water and ethyl acetate. The organic layer was dried (MgSO$_4$) and evaporated to give 3,4-dihydro-5-(4-acetonyloxyphenyl)-6-methyl-2(1H)-pyridinone as a solid.

$^1$H NMR (CDCl$_3$) ppm:
1.85(3H,s); 2.30(3H,s); 2.60(4H,s); 4.58(2H,s); 6.72–7.18(4H,m); 7.90(1H, broad, replaceable by D$_2$O).

EXAMPLE X24

4,4-Dihydro-6-(4-acetonylphenyl)-3(2H)-pyridazinone

A mixture of 4,5-dihydro-6-[4-(2-hydroxypropyl)-phenyl]-3(2H)-pyridazinone (0.23 g) and pyridinium-chlorochromate (0.21 g) in dichloromethane (20 ml) was stirred at ambient tempeature for 18 hr., filtered and evaporated to a gum which was chromatographed on slice gel. Elution with 4% MeOH in CHCl$_3$ gave 4,5-dihydro-6-[(4-acetonyl)phenyl]-3(2H)-pyridazinone as a crystalline solid.

$^1$H NMR (CDCl$_3$) ppm:
2.18(3H,s); 2.38–3.13(4H,m ; 3.70(2H,s ; 7.68(2H,d); 7.68(2H,d); 9.53(1H,s, replaceable by D$_2$O).

EXAMPLE X25

4,5-Dihydro-6-[4(2-hydroxypropyl)phenyl]-3(2H)pyridazinone

A solution of 3-[4-(2-acetoxypropyl)benzoyl]propionic acid (0.8 g) in glacial acetic acid (10 ml) was treated with hydrazine hydrate (1 ml). The resulting solution was stirred and heated under reflux for 1 hr., cooled, diluted with water, and extracted into ethyl acetate. The organic layer was washed with NaHCO$_3$ solution, dried (MgSO$_4$) and evaporated to give 4,5-dihydro-6-[4-(2-acetoxypropyl)phenyl]-3(2H)-pyridazinone as a colourless oil.

$^1$H NMR (CDCl$_3$) ppm:
1.20(3H,d); 1.98(3H,s); 2.30–3.20(6H,m); 5.12(1H,m); 7.10–7.77(4H,m); 9.80(1H,s, replaceable by D$_2$O).

4,5-Dihydro-6-[4-(2-acetoxypropyl)phenyl]-3(2H)pyridazinone (0.73 g) was heated under reflux in 2N sodium hydroxide solution for 2 hr, cooled, neutralised with 2N hydrochloric acid, and extracted into ethyl acetate. The organic extract was dried (MgSO$_4$) and evaporated to an oil which was chromatographed on silica gel. Elution with methanol-chloroform (4:96) gave 4,5-dihydro-6-[4-(2-hydroxypropyl)phenyl]-3(2H)pyridazinone as a white solid.

$^1$H NMR (CDCl$_3$) ppm:
1.15(3H,d); 2.30–3.00 (6H,m); 3.30(1H, broad, replaceable by D$_2$O); 3.95(1H,m); 7.00–7.62(4H,m); 9.50(1H,s, replaceable by D$_2$O).

EXAMPLE X26

3-[4-(2-Acetoxypropyl)benzoyl]propionic acid.

Succinic anhydride (3 g) was added, under a nitrogen atmosphere, to a stirred slurry of aluminium chloride (8.25 g) in 1,2-dichloroethane (50 ml). The resulting mixture was stirred at room temperature for 15 minutes. A solution of 2-acetoxypropyl benzene (5 g) in 1,2-dichloroethane (20 ml) was added, dropwise, to the stirred mixture which was stirred for a further 3 days at room temperature. The reaction mixture was poured into water. The organic solvent was evaporated and the aqueous residue was extracted into ethyl acetate. The organic extract was washed with 2N HCl and extracted into dilute sodium bicarbonate solution. The aqueous extract was acidified with 2N HCl and extracted into ethyl acetate. The organic layer was washed with brine, dried (MgSO$_4$) and evaporated to an oil which was chromatographed on silica gel. Elution with petroleum ether(60-80) - diethyl ether(50:50) gave 3-[4-(2-acetoxypropyl)- benzoyl]propionic acid as an oil.

$^1$H NMR (CDCl$_3$) ppm:
1.21(3H,d); 2.00(3H,s); 2.57–3.42(6H,m); 5.10(1H,m); 7.10–7.92(4H,m); 10.10(1H,s, replaceable by D$_2$O).

EXAMPLE X27

4-benzyloxy-α-[[[2-[4-((4,5-dihydro-1H-2-imidazolyl)methyloxy)phenoxy]-1-methylethyl]amino]methylbenzene methanol.

4-Benzyloxy-α-[[[2-[4-((4,5-dihydro-1H-2-imidazolyl) methyloxy)phenoxy]-!-methylethyl]amino]methyl-benzene methanol was prepared from methyl 4-[2-[(4-benzyloxy-β-hydroxyphenethyl)amino]propyloxy]-phenoxyacetate (2.4 g) and 1,2-diaminoethane (0.5 g) in an analogous manner to the compound described in Example 24.

$^1$H NMR (DMSO-d$_6$) ppm:
1.00(q,3H); 2.55–3.80(m,9H+2H replaceable by D$_2$O); 4.30–4.60(m,3H); 5.07 (s,2H); 6.80–750(m,13H+1H replaceable by D$_2$O).

EXAMPLE X28

3,4-Dihydro-5-(4-acetonylphenyl)-6-methyl-2(1H)pyridone.

Concentrated sulphuric acid (5 ml) was added dropwise to a solution of 4-(4-(2,2-(ethylenedioxy)propyl)-phenyl)-5-oxo-hexane nitrile (3.09 g) in glacial acetic acid (21 ml). The orange solution was allowed to stand at room temperature for 3 days then poured into water and allowed to stand for 2 hr. The solution was extracted with chloroform, the organic layer separated, washed with sodium bicarbonate solution, dried (MgSO$_4$) and evaporated to an oil (2.44 g) which was chromatographed on silica. Elution with chloroform gave 3,4-dihydro-5-(4-acetonylphenyl)-6-methyl-2(1H)-pyridone as an oil.

$^1$H NMR (CDCl$_3$) ppm: 1.85(3H,bs); 2.15(3H,s); 2.6(4H,bs); 3.7(2H,s), 7.1(4H,s), 8.1(1H, broad).

EXAMPLE X29

4-(4-(2,2-(Ethylenedioxy)propyl)phenyl)-5-oxo-hexane nitrile.

A mixture of 4-(2,2-(ethylenedioxy)propyl)phenyl)-propan-2-one (3.5 g), acrylonitrile (0.79 g) and Triton B (0.58 ml) was heated at 70° C. in dioxan for 14 hr. The solvent was evaporated and the residual oil chromatographed on silica. Elution with 1:1 diethyl ether:petrol (40°-60°) gave 4-(4-(2,2-(ethylenedioxy)propyl)-phenyl)-5-oxo-hexane nitrile, 3.09 g, as an oil. $^1$H NMR (CDCl$_3$) ppm:

1.25(3H,s); 2.05(3H,s), 2.1-2.3(4H,m), 2.9(2H,s); 3.55-3.95(5H,m), 7.05(2H,d); 7.25(2H,d).

EXAMPLE X30

4-(2,2-(Ethylenedioxy)propyl)phenyl propan-2-one.

A mixture of 1,4-phenylene bis(propan-2-one), (17.12 g), ethane-1,2-diol (1.72 g) and a trace of 4-toluene sulphonic acid was heated under reflux in benzene for 2 hr. using a Dean and Stark apparatus. The solvent was evaporated and the residue chromatographed on silica. Elution with 1:3 diethyl ether:petrolroleum ether (40-60) gave 4-(2,2-(ethylenedioxy)propyl)phenyl propan-2-one, as a white solid (3.5 g). Further elution gave starting material (12.9 g).

$^1$H NMR (CDCl$_3$) ppm:

1.31(3H,s); 2.12(3H,s); 2.85(2H,s); 3.6(2H,s); 3.74-4.0 (4H,m); 7.1(2H,d); 7.3(2H,d).

EXAMPLE X31

1-[10-(4-Acetonylphenoxy)decyl]pyrazolidin-3-one.

A mixture of 10-(4-acetonylphenoxy)decylbromide, ethylene ketal (3.0 g), potassium carbonate (3.8 g), pyrazolidin-3-one hydrochloride (1.47 g) and potassium iodide (0.5 g) in acetonitrile:water (95:5), was heated under reflux for 3 hr. The reaction mixture was allowed to cool, filtered and the solvent evaporated in vacuo. The residue was dissolved in chloroform, washed with water (2×50 ml), dried (magnesium sulphate), fitered and the solvent removed in vacuo. The residue was dissolved in acetone (50 ml) and treated with 2M hydrochloric acid solution (3 ml) and allowed to stand at room temperature for 3 hr. The solvent was removed in vacuo and the residue was dissolved in chloroform and washed with 1.2M sodium bicarbonate solution (1×50 ml), water (2×50 ml), dried (magnesium sulphate), filtered and the solvent removed in vacuo to give 1-[10-(4-acetonylphenoxy)decyl]pyrazolidin-3-one (0.66 g).

$^1$H NMR (CDCl$_3$) ppm:

1.1-2.1(16H,m); 2.2(3H,s); 2.3-3.0(4H,m); 3.3(2H,m); 3.7(2H,s); 4.0(2H,m); 7.1(4H,dd); 8.0-92(1H, very broad, exchanges with D$_2$O).

EXAMPLE X32

10-(4-Acetonylphenoxy)decyl bromide, ethylene ketal.

A solution of 4-hydroxyphenyl propan-2-one, ethylene ketal (5.26 g) in methanol at room temperature, was treated with sodium (0.66 g) and allowed to stir for 10 minutes. The resulting solution was then added dropwise over 15 minutes to a solution of 1,10-dibromodecane (9.0 g) in methanol under reflux and the reaction mixture heated for 3 h. The mixture was allowed to cool and the solvent was removed in vacuo. The residue was partitioned between diethylether and water, the organic layer separated, dried (magnesium sulphate), and the solvent removed in vacuo to give an oil which was chromatographed on silica. Elution with chloroform gave 10-(4-acetonylphenoxy)decyl bromide, ethylene ketal (3.0 g) as an oil.

$^1$H NMR (CDCl$_3$) ppm:

1.2-2.0 (19H,m); 2.8(2H,s); 3.2-3.7(4H,m); 3.7-4.1(4H,m); 6.8(2H,d); 7.2(2H,d).

EXAMPLE X33

4-(1-Benzyl-1,2,3,6-tetrahydropyridyl)phenylpropan-2-one.

A mixture 1-benzyl-4-[4-(2,2-ethylene dioxypropyl)-phenyl] piperidin-4-ol (3.0 g) and 4-toluenesulphonic acid (1.9 g) in benzene, was heated under reflux for 3 hr. using a Dean and Stark head. The cooled reaction mixture was washed with 1.2M sodium bicarbonate solution (1×50 ml) water, (2×50 ml , dried (magnesium sulphate), filtered, evaporated in vacuo, and chromatographed on silica. Elution with chloroform gave an oil which was dissolved in acetone and treated with 2M hydrochloric acid (5 ml) at room temperature for 4 h. The solvent was removed in vacuo, the residue dissolved in ether, washed with 1.2M sodium hydrogen carbonate (1×50 ml), water (2×50 ml), dried (magnesium sulphate), filtered and evaporated in vacuo to give 4-(1-benzyl-1,2,3,6-tetrahydropyridyl)phenyl propan-2-one, 1.5 g.

$^1$H NMR (CDCl$_3$) ppm:

2.2(3H,s); 2.7(4H,m); 3.2(2H,m); 3.7(4H,s); 6.1(1H,m); 7.0-7.7(9H,m).

EXAMPLE X34

1-Benzyl-4-[4-(2,2-ethylenedioxypropyl)phenyl] piperidin-4-ol

To a solution of (4-bromophenyl)propan-2-one,ethylene ketal (5.14 g) in dry tetrahydrofuran, cooled to −65° C. in a dry-ice/acetone bath and under a nitrogen atmosphere, was added a solution of n-butyllithium (1.4 g) in dry tetrahydrofuran (13 ml), dropwise over 5 minutes. After stirring for 10 minutes a solution of 1-benzyl-4- piperidone (3.78 g) in dry tetrahydrofuran (25 ml) was added dropwise over 15 minutes. The reaction mixture was stirred for 1 h at −65° C. then allowed to come to room temperature. Saturated ammonium chloride solution (40 ml) was added followed by extraction with diethylether. The ether extract was dried, (magnesium sulphate) filtered, evaporated in vacuo and chromatographed on silica. Elution with chloroform: methanol (98:2) gave 1-benzyl-4-[4-(2,2-ethylenedioxypropyl)phenyl] piperidin-4-ol, 6.0 g.

$^1$H NMR (CDCl$_3$) ppm:

1.3(3H,s); 1.4-2.8(9H,m); 2.9(2H,s); 3.6(2H,s); 3.8(4H,m); 7.3(9H,m).

EXAMPLE X35

4-(1,2,3,6-Tetrahydropyridyl)phenyl propan-2-one

4-[4-(2,2-Ethylenedioxypropyl)phenyl piperidin-4-ol (0.9 g) was dissolved in 50% hydrochloric acid solution, and heated under reflux for 4 hr. The solution was cooled, basified with 1.2M sodium bicarbonate solution and extracted with ethylacetate (3×50 ml). The organic extract was dried (magnesium sulphate), filtered and evaporated in vacuo, to give an oil which was chromatographed on silica. Elution with chloroform:methanol (97:3) gave 4-(1,2,3,6-tetrahydropyridyl) phenyl propan-2-one (0.5 g).

$^1$H NMR (CDCl$_3$) ppm:

2.2 (3H,s); 2.3–2.7(2H,m); 2.8–3.7(5H,m); 3.8(2H,s); 6.1 (1H,m); 7.1–7.5(4H,dd).

EXAMPLE X36

4-[4-(2,2-Ethylenedioxypropyl)phenyl]piperidin-4-ol.

1-Benzyl-4-[4-(2,2-ethylenedioxypropyl)phenyl]-piperidin-4-ol (10.7 g) in methanol, was hydrogenated at room temperature and pressure over 10% palladium on carbon (5.0 g). After filtration through celite and evaporation of the solvent in vacuo, the residue was crystallised from ethanol:ether to give 4-[4-(2,2-ethylenedioxypropyl)phenyl]piperidin-4-ol (7.0 g).

$^1$H NMR (DMSO-d$_6$) ppm:

1.2(3H,s); 1.7–2.8(4H,m); 2.9(2H,s); 3.1–3.6(5H,m); 3.9(4H,m); 5.2(1H, broad); 7.1–7.6(4H,dd).

EXAMPLE X37

5-(4-Acetonylphenoxymethyl)-3-hydroxyisoxazole

A solution of (4-hydroxyphenyl)propan-2-one ethylene ketal (1.4 g) in ethanol, was treated with a solution of sodium (0.16 g) in ethanol (25 ml) and heated under reflux for 10 minutes. A solution of 5-chloromethyl-2-(1,2,3,4-tetrahydropyran-2-yl)isoxazol-3-(2H)one (1.5 g) in ethanol was added dropwise, and the reaction was heated for 18 hr. The cooled solution was evaporated in vacuo, the residue partitioned between ethylacetate and water, the organic layer separated, dried (magnesium sulphate), and the solvent removed in vacuo to give an oil which was chromatographed on silica. Elution with ether: 60:80 petrol (1:1) gave an oil which was dissolved in acetone and treated with 2M hydrochloric acid solution (5 ml) and allowed to stand at room temperature for 4 hr. The solvent was removed in vacuo, the residue dissolved in ethyl acetate, washed with 1.2M sodium bicarbonate solution (1×50 ml), dried (magnesium sulphate , filtered and evaporated to give 5-(4-acetonylphenoxymethyl)3-hydroxyisoxazole.

$^1$H NMR (CDCl$_3$) ppm.

2.2 (3H,s); 3.7(2H,s); 4.9 (1H,s); 5.0 (2H,s) 6.0 (1H,s); 6.9–7.4 (4H,dd).

EXAMPLE X38

Methyl 5-[4-acetonylphenoxy]furan-2-carboxylate.

Sodium hydride (1.1 g of an 80% dispersion in oil) was added, with vigorous stirring to a solution of (4-hydroxyphenyl)propan-2-one, ethylene ketal (6.8 g) in dimethylsulphoxide (50 ml). After 30 minutes, methyl 5 nitrofuran-2-carboxylate (5 g) was added and the resulting mixture was stirred and heated at 80°–90° C. for 10 hr. The cooled reaction mixture was poured into ice-water and extracted into diethylether. The organic layer was washed with 5% potassium hydroxide solution and water, dried (MgSO$_4$) and evaporated to an oil which was chromatographed on silica gel. Elution with chloroform gave methyl 5-[4-acetonylphenoxy]-furan-2-carboxylate, ethylene ketal (3.3 g) which was taken up in a 1:1 mixture of methanol and 2N hydrochloric acid and stirred at ambient temperature for 4 hr. Evaporation of the methanol and extraction of the aqueous residue into dichloromethane gave an oil which was chromatographed on silica gel. Elution with chloroform gave methyl 5-[4-acetonylphenoxy]furan-2-carboxylate.

$^1$H NMR (CDCl$_3$) ppm:

2.16(3H,s); 3.66(2H,s); 3.84(3H,s); 5.52(1H,d); 6.95–7.30(5H,m).

EXAMPLE X39

Methyl 5-[4-acetonylphenoxymethyl]furan-2-carboxylate.

Methyl 5-chloromethyl-2-furoate (4.5 g) was added to a mixture of 4-hydroxyphenyl propan-2-one, ethylene ketal (5 g) and potassium carbonate (3.56 g) in acetone (150 ml) containing a catalytic amount of potassium iodide. The reaction mixture was stirred and heated under reflux for 4 hr., cooled and filtered. The filtrate was evaporated to an oil which was purified by column chromatography on silica gel. Elution with chloroform gave a crystalline solid which was stirred at ambient temperature for 4 hr. in a mixture of methanol (50 ml) and 2N hydrochloric acid (50 ml). The methanol was evaporated and the aqueous residue was extracted into dichloromethane. The organic extract was dried (MgSO$_4$) and evaporated to give methyl 5-[4-acetonylphenoxymethyl]furan-2-carboxylate as an oil.

$^1$H NMR (CDCl$_3$) ppm:

2.16(3H,s); 3.67(2H,s); 3.92(3H,s); 5.07(2H,s); 6.57(1H,d); 6.82–7.30(5H,m).

EXAMPLE X40

Methyl 5-[4-[2-[(3-chloro-β-hydroxyphenethyl)amino] propyl]phenoxymethyl]furan-2-carboxamide.

Methyl 5-[4-[2-[(3-chloro-β-hydroxyphenethyl)amino]propyl]phenoxymethyl]furan-2-carboxamide was prepared from methyl 5-[4-acetonylphenoxymethyl]furan-2-carboxamide (1.87 g) and 2-hydroxy-2-(3-chlorophenyl)ethanamine (1.12 g) in an analogous manner to the compound described in Example 50.

$^1$H NMR (CDCl$_3$) ppm:

1.07(3H,d); 2.42–3.00(1 OH,m,2H replaceable by D$_2$O); 4.56(1H,m); 4.95(2H,s); 6.50(1H,d); 6.66–7.30 (1 OH,m,1H,replaceable by D$_2$O).

EXAMPLE X41

Methyl 5-(4-acetonylphenoxymethyl]furan-2-carboxamide.

Methylamine (10 ml of a 33% solution in ethanol) was added to a solution of methyl 5-(4-acetonylphenoxy methyl]furan-2-carboxylate (5 g) in ethanol (30 ml). The mixture was heated at 100° C. in an autoclave for 6 hr., cooled, and evaporated to an oil which was dissolved in a mixture of methanol (50 ml) and 2N hydrochloric acid (50 ml) and stirred at ambient temperature for 3 hr. Evaporation of the solvent and extraction of the residue into dichloromethane gave methyl 5-(4-acetonylphenoxy methyl]furan-2-carboxamide.

$^1$H NMR (CDCl$_3$) ppm:

2.16(3H,s); 2.98(3H,d); 3.68(2H,s); 4.98(2H,s); 6 51(1H,d); 6.83–7.44(6H,m,1H replaceable by D$_2$O).

EXAMPLE X42

2-Amino-5-(4-acetonylphenoxymethyl]-4,5-dihydrooxazole.

A solution of cyanogen bromide (0.88 g) in methanol (100 ml) was added, dropwise, to a stirred solution of (4-acetonylphenoxy)-3-amino propan-2-ol), ethylene ketal (3.62 g) and sodium acetate (1.46 g) in methanol (30 ml). The reaction mixture was stirred at ambient temperature for 20 hr. evaporated, cooled in ice, diluted with 2N sodium hydroxide solution and extrated into chloroform. The organic layer was dried (MgSO$_4$) and evaporated to an oil which was purified by column chromatography on silica gel. Elution with acetonitrile/methanol/ammonia (15:2:1) gave a low-melting solid which was dissolved in a mixture of methanol (30 ml) and 2N hydrochloric acid (30 ml) and stirred at ambient temperature for 4 hr. The methanol was evaporated and the aqueous residue was basified by addition of 2N sodium hydroxide solution, extracted into chloroform, dried (MgSO$_4$) and evaporated to give 2-amino-5-(4-acetonylphenoxymethyl]-4,5-dihydrooxazole.

$^1$H NMR (CDCl$_3$) ppm:
2.14(3H,s); 3.40–415(6H,m,2H replaceable by D$_2$O); 4.33–4.92(3H,m); 6.71–7.16(4H,m).

EXAMPLE X43

Methyl 5-[4-[2-[(3-chloro-β-hydroxyphenethyl)amino] propyl]phenoxymethyl]tetrahydrofuran-2-carboxamide.

Methyl 5-[4-[2-[(3-chloro-β-hydroxyphenethyl)amino] propyl]phenoxymethyl]tetrahydrofuran-2-carboxamide was prepared from methyl 5-[4-acetonylphenoxymethyl]tetrahydrofuran-2-carboxamide and 2-hydroxy-2-(3-chlorophenyl)ethanamine in an analogous manner to the compound described in Example 50.

$^1$H NMR (CDCl$_3$) ppm:
1.10 (3H,d); 1.90–3.15 (15H,m,3H replaceable by D$_2$O); 4.00–4.70 (5H,m); 6.71–7.30 (8H,m).

EXAMPLE X44

Methyl 5-[4-acetonylphenoxymethyl]tetrahydrofuran-2-carboxamide.

Methylamine (15 ml of a 33% solution in ethanol) was added, dropwise, to a stirred solution of methyl 5-[4-acetonylphenoxymethyl]tetrahydrofuran-2-carboxylate, ethylene ketal (4.1 g) in ethanol (80 ml). The reaction mixture was stirred and heated under reflux for 4 hr, cooled and evaporated to an oil which was dissolved in a mixture of methanol (40 ml) and 2N hydrochloric acid (40 ml) and stirred at ambient temperature for 3 hr. The methanol was evaporated and the aqueous residue was extracted into dichloromethane. The organic extract was dried (MgSO$_4$) and evaporated to an oil which was purified by column chromatography on silica gel. Elution with methanol in chloroform (2:98) gave methyl 5-[4-acetonylphenoxymethyl]tetrahydrofuran-2-carboxamide.

$^1$H NMR (CDCl$_3$) ppm:
1.68–2.60 (3H,s plus 4H,m); 2.81 (3H,d); 3.63 (2H,s); 3.82–4.54 (4H,m); 6.75–7.18 (4H, q plus 1H, broad, replaceable by D$_2$O).

EXAMPLE X45

Methyl 5-[4-acetonylphenoxymethyl]tetrahydrofuran-2-carboxylate, ethylene ketal.

Methyl 5-[4-acetonylphenoxymethyl]furan-2-carboxylate, ethylene ketal (12.5 g) was hydrogenated at ambient temperature and pressure, in methanol, in the presence of 5% rhodium on alumina. The reaction mixture was filtered and evaporated to an oil which was purified by column chromatography on silica gel. Elution with chloroform gave methyl 5-[4-acetonylphenoxymethyl]tetrahydrofuran-2-carboxylate, ethylene ketal.

$^1$H NMR (CDCl$_3$) ppm:
1.33 (3H,s); 1.70–2.50 (4H,m,); 2.84 (2H,s); 3.65–3.90 (3H,s plus 4H,m); 3.93–4.65 (4H,m); 6.75–7.28 (4H,q).

Demonstration of Effectiveness of Compounds (I) Anti-obesity Activity.

(a) The test compound was administered by oral gavage in water to genetically obese mice daily for 28 days. At the end of the time the carcass composition was determined. The result obtained was as follows:

| Compound of Example No. | Dose mg/Kg p.o | g lipid/mouse | |
|---|---|---|---|
| | | treated | control |
| 3 | 8.6 | 19.40 | 23.63 |
| 20 | 7.94 | 20.05 | 21.16 |
| 22 | 23.8 | 18.10 | 19.76 |
| 24 | 9.22 | 16.56 | 19.76 |
| 33 | 9.1 | 22.70 | 24.55 |
| 45 | 145* | 19.65 | 20.83 |

*Dose represents mg/kg in diet (b) Female BALB/c mice were trained to feed on powdered oxoid for 1 week. They were then housed in threes and the compound under study was added to the diet for 3 days. Food was removed at 09.00 h and the mice were killed at 11.00 h. The parametrial fat pads were weighed as pairs. The result is a mean of 9 values.

| Compound of Example No. | Dose mg/kg diet | Percentage reduction in weight of parametrial fat pads compared with controls |
|---|---|---|
| 1 | 85 | 40 |
| 3 | 64 | 22 |
| 4 | 200 | 11 |
| 6 | 94 | 13 |
| 7 | 62 | 6 |
| 9 | 112 | 45 |
| 11 | 221 | 16 |
| 15 | 81 | 30 |

(II) Effect on energy expenditure of mice

The effect of the compounds on the energy expenditure of mice was demonstrated by means of the following procedure:

Female CFLP mice each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content, following the principles described by J. B. de V. Weir, J. Physiol. (London) 109, 1–9 (1949). The results are expressed as a percentage of the rate of energy expenditure of the mice dosed with water.

| Compounds of Example No. | Dose mg/kg p.o. | Mean Energy Expenditure | |
|---|---|---|---|
| | | (0–3 h) | (0–21 h) |
| 1 | 8.3 | 110 | 93 |
| 3 | 8.6 | 136 | 115 |
| 9 | 7.8 | 126 | 117 |
| 18 | 22.1 | 146 | 117 |
| 19 | 22.5 | 143 | 109 |

-continued

| Compounds of Example No. | Dose mg/kg p.o. | Mean Energy Expenditure (0–3 h) | (0–21 h) |
|---|---|---|---|
| *20(45:55) | 17.6 | 116 | 108 |
| *20(93:7) | 12.0 | 116 | 104 |
| 21 | 23.8 | 153 | 108 |
| 22 | 23.8 | 164 | 121 |
| 23 | 23.8 | 166 | 121 |
| 24 | 23.0 | 168 | 121 |
| 25 | 22.2 | 110 | 99 |
| 26 | 21.0 | 128 | 115 |
| 27 | 22.0 | 160 | 111 |
| 28 | 20.2 | 129 | 112 |
| 29 | 22.6 | 129 | 110 |
| 30 | 25.6 | 138 | 109 |
| 31 | 26.0 | 145 | 122 |
| 32 | 21.0 | 134 | 96 |
| 33 | 22.7 | 120 | 99 |
| 34 | 21.7 | 105 | 101 |
| 35 | 23.4 | 134 | 108 |
| 36 | 22.0 | 117 | 103 |
| 38 | 20.1 | 126 | 105 |
| 40 | 20.7 | 137 | 110 |
| 41 | 19.7 | 109 | 103 |
| 42 | 19.3 | 123 | 107 |
| 43 | 19.9 | 130 | 109 |
| 44 | 21.1 | 143 | 101 |
| 45 | 36.3 | 145 | 109 |
| 48 | 19.3 | 112 | 110 |
| 49 | 23.3 | 144 | 114 |
| *50(19:81) | 22.2 | 121 | 101 |
| *50(55:45) | 22.2 | 126 | 102 |
| 51 | 25.1 | 132 | 110 |
| 52 | 28.1 | 114 | 98 |
| 53 | 26.2 | 130 | 110 |

*Relates to diastereoisomer % ratio.

(III) Effect on Energy Expenditure of Rats

The effect of the compounds on the energy expenditure of rats was demonstrated by means of the following procedure:

Male Sprague-Dawley rats each weighing between 170–200 g were deprived of food for 16 hours before, and during the experiment. Water was provided ad lib at all times. The compounds were administered orally in water to 3 or 4 rats. A further 4 rats were dosed orally with water. The rats were placed in boxes through which air was drawn and the oxygen content of the air leaving the boxes was measured. The energy expenditure of the rats was calculated for 3 hours and for 21 hours after dosing from the volume of air leaving the boxes and its oxygen content, following the principles described by J. B. de V. Weir, J. Physiol. (London) 109, 1–9 (1949). The results are expressed as a percentage of the rate of energy expenditure of the rats dosed with water.

| Compound of Example No. | Dose mg/kg p.o. | Mean Energy Expenditure (0–3 h) | (0–21 h) |
|---|---|---|---|
| 1 | 4.25 | 125 | 115 |
| 2 | 4.16 | 116 | 106 |
| 3 | 8.6 | 137 | 131 |
| 4 | 20.0 | 108 | 103 |
| 5 | 4.3 | 137 | 120 |
| 6 | 4.7 | 138 | 111 |
| 7 | 20.7 | 121 | 113 |
| 8 | 18.1 | 118 | 110 |
| 9 | 7.55 | 117 | 114 |
| 10 | 10.04 | 121 | 116 |
| 11 | 8.86 | 111 | 108 |
| 12 | 8.22 | 130 | 110 |
| 13 | 9.59 | 121 | 128 |
| 14 | 9.50 | 112 | 110 |
| 15 | 8.00 | 134 | 112 |
| 16 | 4.86 | 108 | 107 |
| 17 | 24 | 114 | 107 |
| 18 | 4.0 | 113 | 117 |
| 19 | 4.1 | 120 | 119 |
| 21 | 4.8 | 140 | 131 |
| 22 | 4.8 | 113 | 115 |
| 23 | 4.8 | 128 | 121 |
| 24 | 2.3 | 120 | 115 |
| 28 | 4.0 | 148 | 123 |
| 33 | 4.5 | 108 | 108 |
| 34 | 8.6 | 129 | 107 |
| 35 | 4.7 | 119 | 111 |
| 36 | 8.8 | 119 | 99 |
| 37 | 4.9 | 113 | 111 |
| 40 | 4.1 | 105 | 105 |

(IV) Hypoglycaemic activity

Female CFLP mice, weighing approximately 25 9, were fasted for 24 hours prior to the study. The compounds under study were administered orally as an aqueous solution to each of the 6 mice. 30 minutes later a blood sample (20 μl) was obtained from the tail for the analysis of blood glucose. Immediately after taking this blood sample, glucose (1 g/kg body weight) was administered subcutaneously to each mouse. 6 mice were given water as a control. Blood samples were then obtained from each mouse at 30 minute intervals for 120 minutes.

Compounds that produced a significant ($p<0.05$) reduction of blood glucose, compared with control mice given water, at any time interval, were considered active. The area under the blood glucose curve over the 2 hour period after the administration of the glucose was calculated for each compound and compared with the value for control animals.

| Compounds of Example No. | Dose μmol/kg | % Reduction in Area under Blood Glucose Curve |
|---|---|---|
| 1 | 2.5 | 44 |
| 4 | 25 | 11 |
| 5 | 2.5 | 39 |
| 6 | 12.5 | 9 |
| 7 | 1.0 | 47 |
| 8 | 1.0 | 45 |
| 9 | 2.5 | 28 |
| 18 | 5 | 26.5 |
| 19 | 1 | 14 |
| 21 | 5 | 44 |
| 22 | 1 | 10 |
| 23 | 1 | 13 |
| *30(55:45) | 25 | 29 |
| 31 | 1 | 27 |
| 32 | 25 | 5 |
| 33 | 12.5 | 5 |
| 35 | 12.5 | 27 |
| 37 | 2.5 | 12 |
| 38 | 5 | 20 |
| 42 | 12.5 | 9 |

*Relates to diastereoisomeric ratio.

We claim:

1. A compound of the general formula (I):

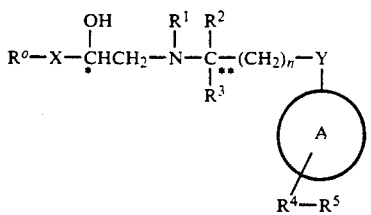

or an in vivo hydrolyzable pharmaceutically acceptable ester thereof; or a pharmaceutically acceptable salt thereof, wherein $R^0$ represents a phenyl or naphthyl group which is unsubstituted or substituted with up to five substituents compounding a halogen, alkyl, phenyl, alkoxy, haloalkyl, hydroxy alkyl, hydroxy, amino, nitro, carboxy and pharmaceutically acceptable salts, esters and amides thereof, alkoxycarbonyl, alkoxycarbonyl alkyl alkylcarbonyloxy, or alkylcarbonyl, group; or a benzofuranyl group, which is unsubstituted or substituted with an alkyl group, X represents a bond or $-O-CH_2$, $R^1$ represents a hydrogen atom or a moiety

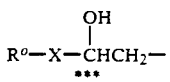

wherein $R^0$ and X are as defined above;

$R^2$ and $R^3$ independently represent a hydrogen atom or a straight or branched chain alkyl group having up to 12 carbon atoms, n represents an integer 1 or 2, Y represents a bond or a moiety $-CH_2-O-$, moiety Ⓐ represents a phenyl or naphthyl group, $R^4$ represents a bond or an oxygen atom or $-R^{4A}$ or a moiety $-O-R^{4A}-$, or a moiety $-R^{4A}-O-$, wherein $R^{4A}$ represents a $C_{1-12}$ alkylene group, a $C_{1-12}$ alkyenylene group or a $C_{1-12}$ alkynylene group, and $R^5$ represents a thiazolidine -2,4-dione group, which is unsubstituted or substituted by alkyl; hydroxy; alkoxy; oxo; amino; alkanoyl amino; mono- and di- alkyl amino; mono- and di-alkylaminoalkyl; fluoro, chloro, bromo; carboxy and pharmaceutically acceptable salts, esters and amides thereof; alkanoyloxy, phenyl, naphthyl, phenylalkyl, or naphthylalkyl, wherein the phenyl or naphthyl ring is optionally substituted as in variable $R^0$.

2. A compound according to claim 1 wherein $R^4$ represents $C_{1-12}$ alkylene group.

3. A compound according to claim 1 wherein $R^4$ represents $(-CH_2-)$.

4. A compound according to claim 1, selected from the group consisting of:
5-[4-[2-[($\beta$-4-dihydroxyphenethyl)amino]propyl]benzyl]thiazolidine-2,4-dione;
5-[4-[2-[(3-chloro-$\beta$-hydroxyphenethyl)amino]propyl]-benzyl]thiazolidine-2,4-dione;
5-[4-[2[(4-amino-3,5-dichloro-$\beta$-hydroxyphenethyl)-amino]propyl]benzyl]thiazolidine-2,4-dione;
or a pharmaceutically acceptable ester thereof; or a pharmaceutically acceptable salt thereof.

5. A compound according to claim 1, represented by formula (II):

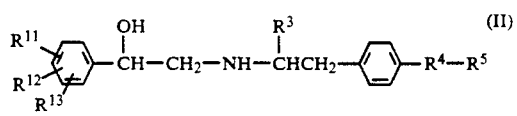

or a pharmaceutically acceptable ester thereof; or a pharmaceutically acceptable salt thereof, wherein $R^3$, $R^4$ and $R^5$ are as defined in relation to formula (I) and $R^{11}$, $R^{12}$ and $R^{13}$ each independently represent hydrogen; halogen, amino, hydroxy or hydroxymethyl.

6. The compound according to claim 5, wherein the halogen is chlorine.

7. A pharmaceutical composition comprising a compound of formula (I) as defined in claim 1, or a pharmaceutically acceptable ester thereof; or a pharmaceutically acceptable salt thereof and a pharmaceutically acceptable carrier therefor.

8. A method for the treatment of obesity or hyperglycaemia in a human or non-human animal which method comprises administering an effective, non-toxic, amount of a compound of formula (I) as defined in claim 1 or a pharmaceutically acceptable ester thereof; or a pharmaceutically acceptable salt thereof to a hyperglycaemic human or non-human animal.

9. A method for increasing weight gain, improving the feed utilisation efficiency, increasing lean body mass, decreasing birth mortality rate and increasing the post-natal survival rate of livestock, which method comprises the administration to livestock of an effective non-toxic amount of a compound of formula (I) as defined in claim 1 or a veterinarily acceptable ester thereof; or a veterinarily acceptable salt thereof.

* * * * *